(12) United States Patent
Sethumadhavan et al.

(10) Patent No.: US 9,032,513 B2
(45) Date of Patent: May 12, 2015

(54) SYSTEMS AND METHODS FOR EVENT STREAM PLATFORMS WHICH ENABLE APPLICATIONS

(71) Applicants: Vishnuvyas Sethumadhavan, Mountain View, CA (US); Anthony Michael LaRocca, San Francisco, CA (US); Shahram Shawn Dastmalchi, San Ramon, CA (US); Robert Derward Rogers, Pleasanton, CA (US); Shamshad Alam Ansari, San Mateo, CA (US); Imran N. Chaudhri, Potomac, MD (US)

(72) Inventors: Vishnuvyas Sethumadhavan, Mountain View, CA (US); Anthony Michael LaRocca, San Francisco, CA (US); Shahram Shawn Dastmalchi, San Ramon, CA (US); Robert Derward Rogers, Pleasanton, CA (US); Shamshad Alam Ansari, San Mateo, CA (US); Imran N. Chaudhri, Potomac, MD (US)

(73) Assignee: Apixio, Inc., San Mateo, CA (US)

( * ) Notice: Subject to any disclaimer, the term of this patent is extended or adjusted under 35 U.S.C. 154(b) by 0 days.

(21) Appl. No.: 13/783,289

(22) Filed: Mar. 2, 2013

(65) Prior Publication Data
US 2013/0238349 A1    Sep. 12, 2013

Related U.S. Application Data

(63) Continuation-in-part of application No. 13/223,228, filed on Aug. 31, 2011, and a continuation-in-part of application No. 13/747,336, filed on Jan. 22, 2013.

(60) Provisional application No. 61/379,228, filed on Sep. 1, 2010, provisional application No. 61/590,330, filed on Jan. 24, 2012, provisional application No. 61/600,994, filed on Feb. 20, 2012.

(51) Int. Cl.
*G06F 17/16* (2006.01)
*G06F 19/00* (2011.01)
*G06Q 50/22* (2012.01)
*G06Q 50/24* (2012.01)
*G06F 17/27* (2006.01)

(52) U.S. Cl.
CPC .............. *G06F 19/327* (2013.01); *G06Q 50/22* (2013.01); *G06F 19/322* (2013.01); *G06Q 50/24* (2013.01); *G06F 19/328* (2013.01)

(58) Field of Classification Search
CPC . G06F 19/322; G06F 19/328; G06F 21/6245; G06F 17/18; G06F 19/3443; G06F 19/3487
See application file for complete search history.

(56) References Cited

U.S. PATENT DOCUMENTS

2010/0228721 A1* 9/2010 Mok et al. ...................... 707/711
2010/0324936 A1* 12/2010 Vishnubhatla et al. ........... 705/3

* cited by examiner

*Primary Examiner* — Venkat Perungavoor
(74) *Attorney, Agent, or Firm* — Kang S. Lim

(57) ABSTRACT

Systems and methods to generate a final event stream are provided. The system collects information from a wide variety of sources, and then parses, normalizes, and indexes the information. This generates an initial event stream that can be tagged and then iteratively processed to generate a final event stream. The processing includes first order logic querying and knowledge extraction to infer additional events which is added to the event stream. The final event stream is used by a knowledge exchange for consumption by applications. These applications may be internal applications and/or third party applications. This system may be particularly useful in use with medical information, or any other big data enterprise system.

20 Claims, 33 Drawing Sheets

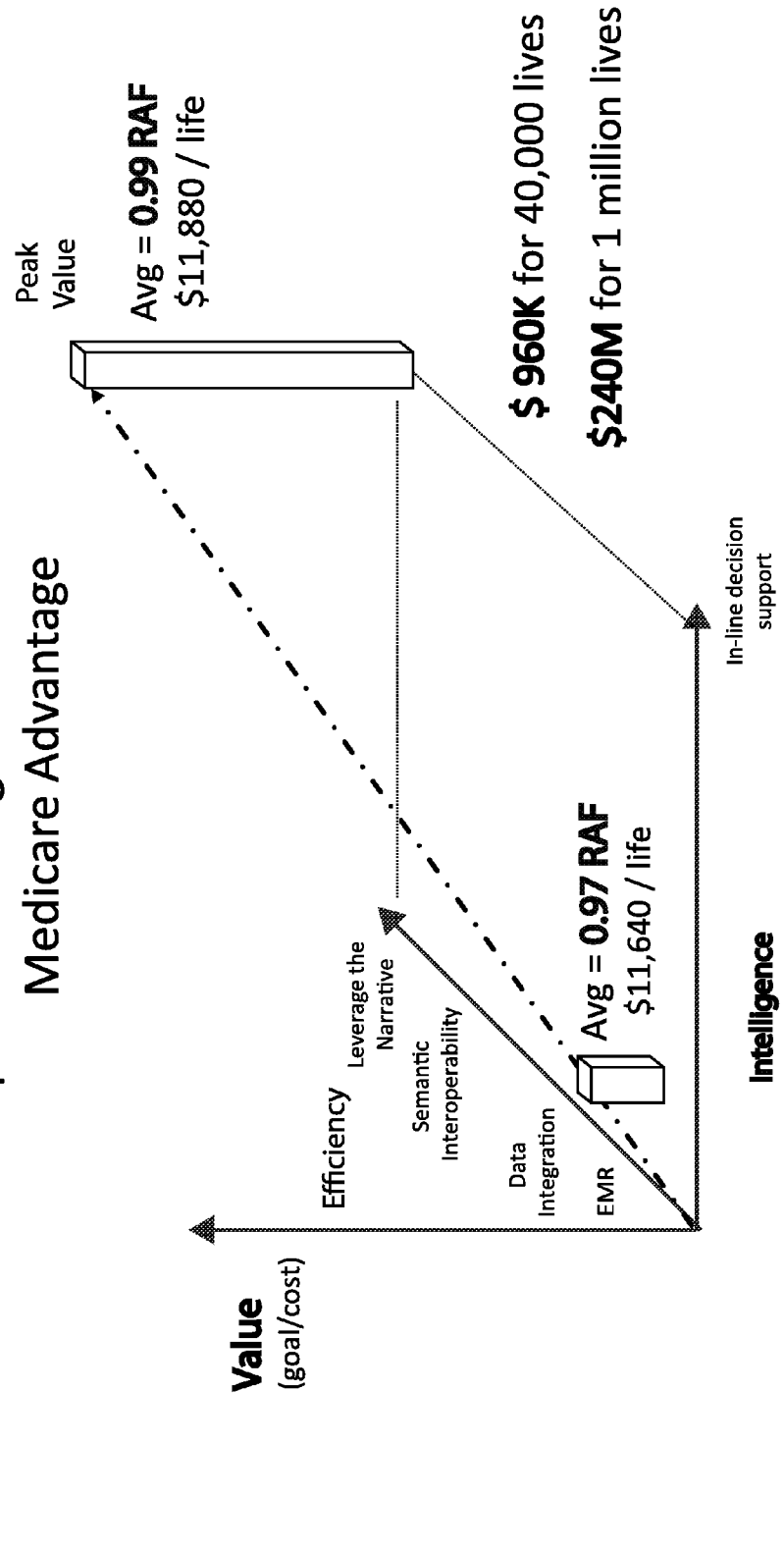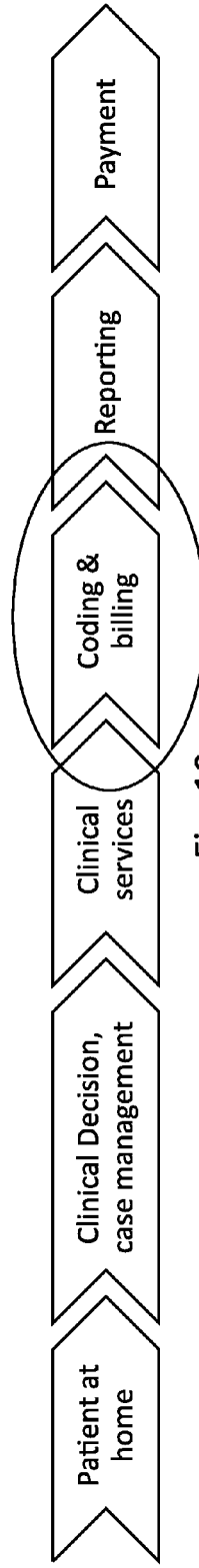
Fig. 10

Joan Sample × mi    Search

| Coded Data | | Coded Data |
| Free Text | | Free Text |
| Scanned Documents | | Scanned Documents — 73 years old. You are aware of his coronary heart disease, acute myocardial infarction four years ago, and drug-eluting stents in his right coronary. |
| EHR #1 | | EHR #2 |

Fig. 14

SYSTEMS AND METHODS FOR EVENT STREAM PLATFORMS WHICH ENABLE APPLICATIONS

CROSS REFERENCE TO RELATED APPLICATION

This continuation-in-part application claims the benefit of application Ser. No. 13/223,228 filed on Aug. 31, 2011, entitled "Medical Information Navigation Engine (MINE) System", which application claims priority to U.S. Provisional Application No. 61/379,228 filed on Sep. 1, 2010, of the same title, both applications are incorporated herein in their entirety by this reference.

Additionally, this continuation-in-part application claims the benefit of application Ser. No. 13/747,336 filed on Jan. 22, 2013, entitled "Knowledge Extraction and Exchange Method and Apparatus", which application claims priority to U.S. Provisional Application No. 61/590,330 filed on Jan. 24, 2012, of the same title, both applications are incorporated herein in their entirety by this reference.

This continuation-in-part application also claims the benefit of U.S. Provisional Application No. 61/600,994 filed on Feb. 20, 2012, entitled "Clinical Knowledge Extraction, Provider-Guided Educational Material and Top of Mind Concepts for Patient", which application is incorporated herein in its entirety by this reference.

BACKGROUND

The present invention relates generally to the generation of "events" and ultimately a collection of events, referred to as an "event stream". Events and event streams, in the context of this disclosure, are applicable whenever large and distributed data records are being managed and are subject to heightened privacy or security. In particular, such systems and methods are applicable to the healthcare field, where federal and state laws restrict data in the interest of patient privacy. Such event streams enable platforms for applications, such as analytics, business intelligence, revenue cycle management, utilization management and quality applications.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is the number of sources of information, the great amount of information from each source, maintenance of data in a HIPAA compliant manner, and consolidation of such information in a manner that renders it meaningful and useful to those in the field in addition to patients. Obviously, this has contributed to increased medical costs and is perhaps largely attributed to the field suffering from an organized solution to better aid the medical professionals, to better aid those requiring more reliable patient history and those requiring more control and access over such information.

The concept of "big data" is already well established in the field of information technology. Big data is a collection of tools, techniques and methodologies used when data sets are large and complex that it becomes difficult or impossible to store, query, analyze or process using current database management and data warehousing tools or traditional data processing applications. The challenge of handling big data include capture, curation, storage, search, sharing, analysis and visualization. The trend to larger data sets is due to the proliferation of data capture devices and the ease of capturing and entering data from a wide variety of sources.

Due to the intrinsic issues prevalent with medical information—where very large amounts of clinical and administrative information are generated and stored as unstructured text and scanned documents, big data platforms and analysis is all but unheard of. However, the inability to leverage the entirety of the data results in considerable value being lost by healthcare providers, insurance companies, and patients. For example, a big data platform could enable solutions utilizing all of the data to optimize accurate risk assessment, population health, and revenue for value-based healthcare organizations. Without such a platform, these value added solutions are less obtainable.

It is therefore apparent that an urgent need exists for a standardized way of treating, understanding and analyzing all data, including but not limited to clinical, administrative, billing, utilization, revenue and self-reported data that enables downstream applications for the medical field. Such a system will increase care efficiency and increase care quality, provide risk optimization, and increase revenue for value-based healthcare organizations. Apixio's Event Stream platform provides a standardized way of treating, understanding and analyzing all of enterprise data to enable downstream applications.

SUMMARY

To achieve the foregoing and in accordance with the present invention, systems and methods for managing medical information are provided. In particular, systems and methods for the generation of an event stream platform are provided. An event stream platform enables big data analytics and downstream access of a vast dataset of clinical, administrative, billing and other medical events, demographic, behavioral and other information about a patient, provider or a healthcare organization for consumption by applications.

In some embodiments, the systems and methods disclosed herein are designed to generate a final event stream, by collecting medical information from a wide variety of sources. Some of this medical information may not be readable by a computer system, and may require optical character recognition before being further processed. Once all the data is usable, the system may parse, normalize, and index the medical information. This generates an initial event stream that can be tagged and then iteratively processed to generate a final event stream. The processing may be performed by agents, and includes first order logic querying and knowledge extraction to infer additional events which is added to the event stream. The final event stream is one which does not change after additional iterative processing.

In some embodiments, an event is a machine-based language or a data structure that includes a subject, evidence used to infer the event, a fact that was inferred from the evidence, a start date of the event, an end date of the event, an episode level grouping, the source of the event, type of the event, named attributes and values, a snippet of the source, an event classification, an optional parent event and expiry information.

Once the final event stream is generated, it may be provided to a clinical knowledge exchange. In some embodiments, the final event stream might be projected by transformations including, but not limited to, "rolling up" (grouping and aggregating, for example by or to a node within a knowledge graph), filtering, et cetera, before sending it to a clinical knowledge exchange. The clinical knowledge exchange transforms and provides access to the final event stream for consumption by applications. These applications may be internal applications and/or third party applications.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIGS. 9-11 each show a graph of the intelligence, shown in the x-direction, versus value, shown in the y-direction, of various performance improvements realized using the various methods and embodiments of the invention;

FIGS. 12-18 show an example of a patient/user, Joan Sample, benefiting from the process of extracted information used to determine potential conditions, in accordance with a method of the invention;

DETAILED DESCRIPTION

Figure 1:
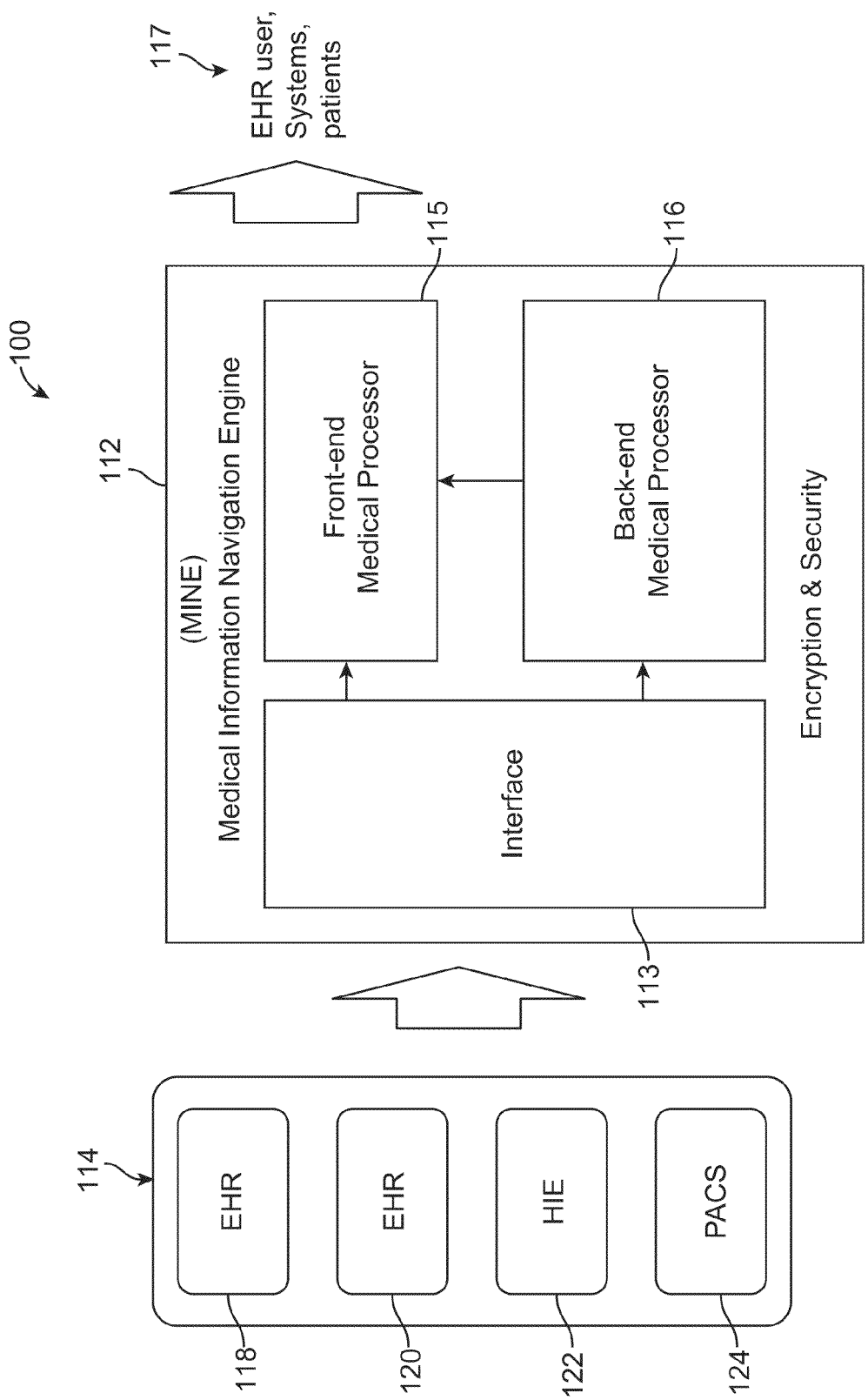
FIG. 1 shows a medical system, in accordance with some embodiments.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

The present invention relates to the generation of "events" and ultimately a collection of events, referred to as an "event stream". Events, as used in this application, are defined as facts (something that is true or false) which are optionally associated with attributes and values that have occurred in a specific time interval for a specific subject (in the clinical context, it could be the patient, an organization, etc.), attributed to a specific agent (i.e. a cause—could be a provider, organizations, device, etc., or a some combination of them), a source (original source of where that fact originated from), and an episode grouping (typically an encounter in the clinical context). An event can also be associated with a collection of attributes with values. An "event stream" is a collection, or set, of such events.

Note that while much of the discussion contained herein relates to the management and big data analysis of medical records, events and event streams in the context of this disclosure are applicable whenever large and distributed data records are being managed and are subject to heightened privacy or security. For example, the disclosed system is a flexible, highly-scalable big-data enterprise system that understands concepts, and associations and relationships between the concepts from unstructured text using machine learning and nlp techniques. The system is completely language independent and domain independent as it extracts the concepts and relationships directly from its input text. Thus, the event streams can be constructed and utilized as across multilingual documents (and thus also serve as a translational tool) and can also be utilized across multiple domains (e.g.: Healthcare, Legal, etc.). Event Streams may thus include different types of data. In fact, even in healthcare, the data does not all need to be medical in nature. The data can be of variety of types including administrative, workflow, process, inventory, lifestyle, technology, etc. As such it is considered that any situation where big data analysis is desirable may be within the scope of this disclosure. Note, however, that the discussion contained herein will primarily be centered on medical information for the sake of clarity and specialized examples.

The following description of some embodiments will be provided in relation to numerous subsections. The use of subsections, with headings, is intended to provide greater clarity and structure to the present invention. In no way are the subsections intended to limit or constrain the disclosure contained therein. Thus, disclosures in any one section are intended to apply to all other sections, as is applicable.

I. Medical Systems

To facilitate the discussion, FIG. 1 illustrates a medical system 100, in accordance with an embodiment of the invention. The system 100 is shown to include medical source 114, a medical information navigation engine (MINE) 112, and medical information consumers (also referred to herein as "output" or "medical output") 117. The medical source 114 are shown to include an electronic health record (EHR) 118, EHR 120, health information exchange (HIE) 122, and a picture archiving and communication system (PACS) 124.

The MINE 112 is shown to include interface 113, a back-end medical processor 116, and a front-end medical processor 115.

The MINE 112 disclosed herein, is capable of receiving medical information data, and de-duplicating, indexing and tagging the data in order to generate an initial event stream. "Medical information", as used herein, refers to any health-related information, including but not limited to patient medical records, patient entered information, care team entered information, healthcare device generated information, and billing information.

Figure 2:
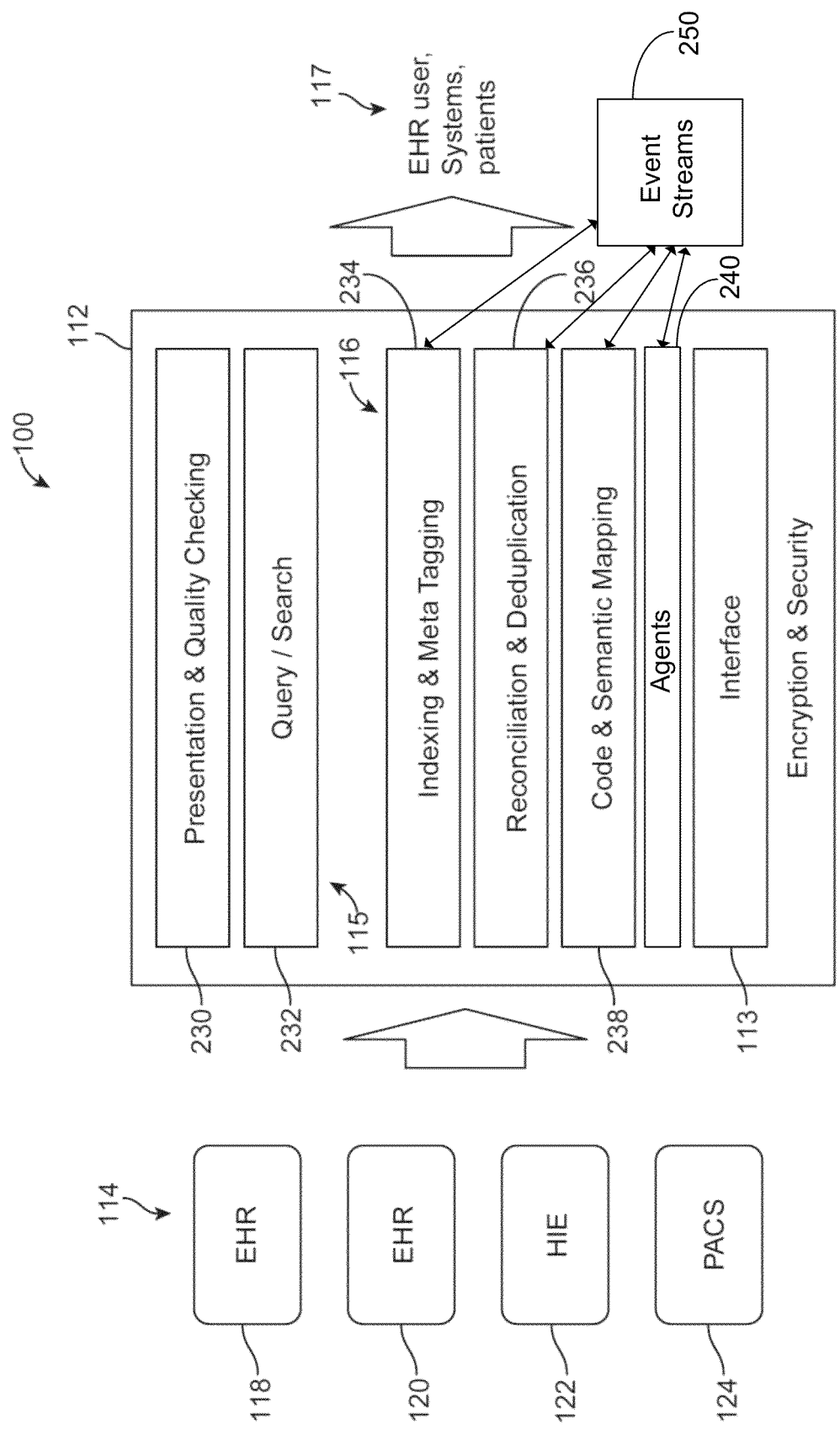
FIG. 2 shows further details of the system, particularly the MINE thereof, in accordance with some embodiments.

A host of "agents" depicted in FIG. 2, which may also be embodied within the MINE 112, may consume the initial event stream, and subsequent event streams, in order to generate a final event stream. The final event stream may then be usable by subsequent applications.

An "agent", as used in the context of this application, is any process that consumes an event stream, along with other external sources of knowledge (such as dictionaries, machine learning models, etc.) and creates new inferred events that are added to the original event stream. Agents may act iteratively on an event stream, where one agent consumes the event stream and adds inferred events to it form a secondary event stream. Then a second agent may consume the secondary event stream and infer yet other events to form a tertiary event stream. Then the first agent may consume the tertiary event stream to form yet another version of the event stream.

Agents utilize knowledge extraction, and/or first order logic (a.k.a. first order predicate calculus) queries over the event streams in order to generate the inferred events. Greater detail is provided below regarding the knowledge extraction and querying abilities of the agents.

Eventually, a final event stream may be generated where the agents have no further events to add to the stream. This final event stream may be then made available to subsequent applications for downstream analytics, such as quality measures, care optimization, etc.

The source 114 generally provides various medical information to the MINE 112. For example, the EHRs 118 and 120 each may provide information such as medical records and billing, the HIE 122 may provide information such as medical records, and the PACS 124 may provide information such as diagnostic imaging and reports.

The medical information consumers 117, which may be made of a host of entities or individuals, such as patients, clinics, medical institutions, health organization, and any other medical-related party, use information that is provided by the processor 115 of MINE 112 and that can, by way of example, consist of patients, medical systems, medical organization administrators, medical researchers, and/or EHR users. For example, user-customized processed medical information (indexed and tagged into an event stream, and inferences generated by agents) is provided by the processor 115 to a number of users within the medical information consumers 117. In this case, the processor 115 generates user-customized processed medical information to a plurality of users, with at least a portion of the user-customize processed medical information being provided to each of the users based on the relevancy of the portion being provided of each user's specific function or role and each user's associated security privileges.

The processor 116, in some embodiments, indexes identifies, maps, and consolidates medical information, received from the interface 113, and tags this information, and determines to reconcile the tagged information. In some methods and embodiments, information that is extracted from images is tagged to enhance recall of search queries. Indexing, at least in part, processes document and converts them into formats that allows for quick searching across a large collection of documents. These processes generate one or more initial event streams, which are then subject to consumption by one or more agents.

The information in the MINE 112 is encrypted and secure to ensure privacy of sensitive medical information. Likewise, any final event streams provided to downstream applications may be encrypted or otherwise anonomized in order to comport to HIPAA and other privacy regulations.

It is understood that the sources 114 of FIG. 1 includes merely some examples of the sources that communicate with the MINE 112 and that other sources, known to those in the field, are contemplated. Similarly, the output 117 may be used by those or entities not discussed herein but that are contemplated and within the scope and spirit of the invention.

The interface 113 serves to receive information that is in various forms, such as but not limited to text, html, CCD, CCR, HL7 and any other type or formatted information. The interface 113 then provides to the processors 115 and 116 information, as needed.

The processor 116 receives some of the medical information that the interface 113 processes and performs certain tasks to process it, such as indexing, semantic meta-tagging, and reconciliation to generate the initial event stream. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

One aspect of consolidation, reconciliation and de-duplication, generally refers to removing of redundant patient medical records, such as, multiple records for the same individual appearing as though the records are for different individuals or multiple data elements that are recorded similarly but slightly differently in the different sources. In this case, the processor 116 recognizes that the records belong to a single individual or are the same data and just recorded differently and automatically consolidates them. The patient or a user of the system 100 may also manually perform reconciliation. The processor 116 advantageously determines whether or not reconciliation is performed.

The processor 116 outputs the indexed, tagged and reconciled information (an event stream) to the processor 115. The foregoing tasks are a generalization and further details of each are provided below.

The processor 115 performs certain tasks on the information provided by the interface 113 and the processor 116, which include query, search, presentation, and quality checking (agent actions). The output of the processor 115 is a final event stream, or output 117.

The MINE 112, through the processor 115, in some embodiments and methods, invites members of a medical care team to join it thereby allowing distributed user-organized care teams.

Querying, as performed by the processor 115, is the ability to receive, as input, a free text query, from a user, (i.e., a query without any restrictions on the structure)—and converting the free text query into commands to a medical search engine, such as Medical Lexical Search Engine and the MATRIX (Medical Application Terminology Relationship IndeX) Concept Search Engine, using a sophisticated query processing engine optimized to work with medical queries. The results of the search engine are sent to the presentation display planner—which decides the most relevant presentation given the user's organization and role (e.g. the provider, search query program, a healthcare administrator, a study administrator, and the patient). The presentation discussed below, receives such information. In some embodiments and methods, the medical information or user information is processed to suggest relevant queries. Queries may be utilized by agents to generate inferred events that may be added to the event stream.

Search, as performed by the processor 115, is built around the concept of Zero-Click Relevance—or the ability to get to all the relevant information an actor in the healthcare system requires by typing in just a single query. The search engine, within the processor 115, performing the search comprises an indexing and searching, as will become apparent shortly. Optionally, search results may be securely embedded into third party programs. In some embodiments, searching involves determining presenting (also referred to herein as "providing") access to specific relevant data based on a search query, the patient, and the user's specific function and/or role and security privileges. A user may be within the output 117 and security privileges are either determined by the MINE 112 or by the patient or both. The information that is uploaded to the MINE 112 by users, such as in output 114 (in some embodiments) is searched by the processor 115. The uploaded information may include information such as but not limited to status posts, records, and images. Such user-uploaded information is routed automatically to the output 117, as needed.

Some aspects of the search are now discussed relevant to an example. Assuming, by way of example, that Dr. Smith, an internal medicine physician, sees a new patient, Joan Sample, who presents with a complaint of chest pain. Joan has brought several continuity-of-care documents (CCDs) and a 600-page pdf file representing of her medical chart. She has seen a cardiologist who uses NextGen's electronic medical record (EMR) and a gastroenterologist who uses eMD's EMR and she has recently visited a local emergency room. Dr. Smith uses the search of the various methods and embodiments of the invention to efficiently assemble the relevant information he needs. Dr. Smith selects Joan Sample as the patient and enters the clinical context "chest pain" in the search bar of a screen presented by the MINE 112 (examples of such screens are shown in subsequent figures herein). He is presented with relevant lab results, such as CKMB, troponin, and amylase, relevant diagnostic results, such as prior electrocardiograms (EKGs) and the most recent chest computed tomography (CT) scan; and all progress notes and consult reports in which concepts relevant to chest pain, like "GERD" and "cardiac stress test", are mentioned. Two distinct types of searches are combined, in accordance with a method and embodiment of the invention, to retrieve information medically relevant to Joan's complaint: 1) Lexical search, where text in the patient record is searched for occurrences of the search term, its variants and synonyms; and 2) Medical concept search, where data that is medically related to the search term is retrieved. Medical concept search finds relevant structured data with standardized codes, such as lab results, and text results, such as progress notes, which include terms medically related to the search term. In Joan's case, a search for "chest pain" returns a CKMB lab result and a reference to the most recent chest CT scan. Accordingly and advantageously, the Lexical and Medical concept search solves Dr. Smith's information overload problem by returning information in the chart most relevant to determining the etiology of Joan's chest pain complaint. Further, in some embodiments, the presentation, discussed shortly, presents a united view of Joan's history by reconciling and de-duplicating data from multiple sources that may be coded and described differently. Redundant data is automatically reconciled even if it is described differently by differently sources.

Presentation, as performed by the processor 115, is displaying health information to the requesting user in a way that reduces the number of clicks and maximizes the amount of meaningful information delivered based on the interpreting the intent of the user query.

Quality checking, as performed by the processor 115, is checking of the quality of medical information provided by various sources, i.e. source 114, by the patients, structured data, and unstructured data, in a Wiki-like mannered setting whereby the users can help maintain and improve the quality of information displayed. The foregoing tasks, performed by the processor 115, are further described in detail below. Additionally, the users or patients may make comments regarding medical information, in a Wiki-like manner.

In summary, the MINE 112 transacts medical information including the interface 113 receiving medical information from a number of medical sources (such as within the source 114) for processing, identifying, mapping, and consolidating by the medical processor 116, providing access to specific relevant data, based on a user's security privileges, within the identified, mapped, and consolidated medical information, based on user-specific functions or roles, performed by the processor 115, and generating user-customized processed medical information to a number of users, such as within the output 117, with at least a portion of the user-customized processed medical information being provided to each of the users based on its relevancy to each user's specific function or role and each user's associated security privileges.

FIG. 2 shows further details of the system 100, particularly the MINE 112 thereof. That is, the processor 116 is shown to include an indexing and metal tagging module 234, which includes an indexing module and a meta tagging module (both of which are not shown in FIG. 2 in the interest of clarity), which may be a module, as shown in FIG. 2 or two physically separate modules. The processor 116 is further shown to include a reconciliation and de-duplication module 236, which also can be broken out into two modules, a reconciliation module and a de-duplication module, and a code and semantic mapping module 238, which also may be a single module or multiple modules. These modules may take the initial event stream and modify or add events to refine the event stream 250. The output of the tagging module, reconciliation and semantic mapping is an initial event stream 250.

Additionally, agents 240 may be included in the processor 116. The agents 240 may make inferences via queries and knowledge extraction of the event streams to generate inferred events. These inferred events may be added to the event streams 250 to further refine the output 117. The modules 234, 236, 238 and 240 may communicate with one another.

The processor 115, in some embodiments, includes display and visualization 340 executing on one or more servers 238, which may be any suitable computing engine, similar to the servers 232, including but not limited to PCs or servers. The display 340 is used to construct presentation and display information to users, such as the patient's records, billing information, and other types of medical information. The display 340, in some embodiments, also performs processing of some of the functions of the processor 115.

The foregoing modules may be software programs, executed by a computer or computing engine of suitable sorts, or may be implemented in hardware.

Figure 3:
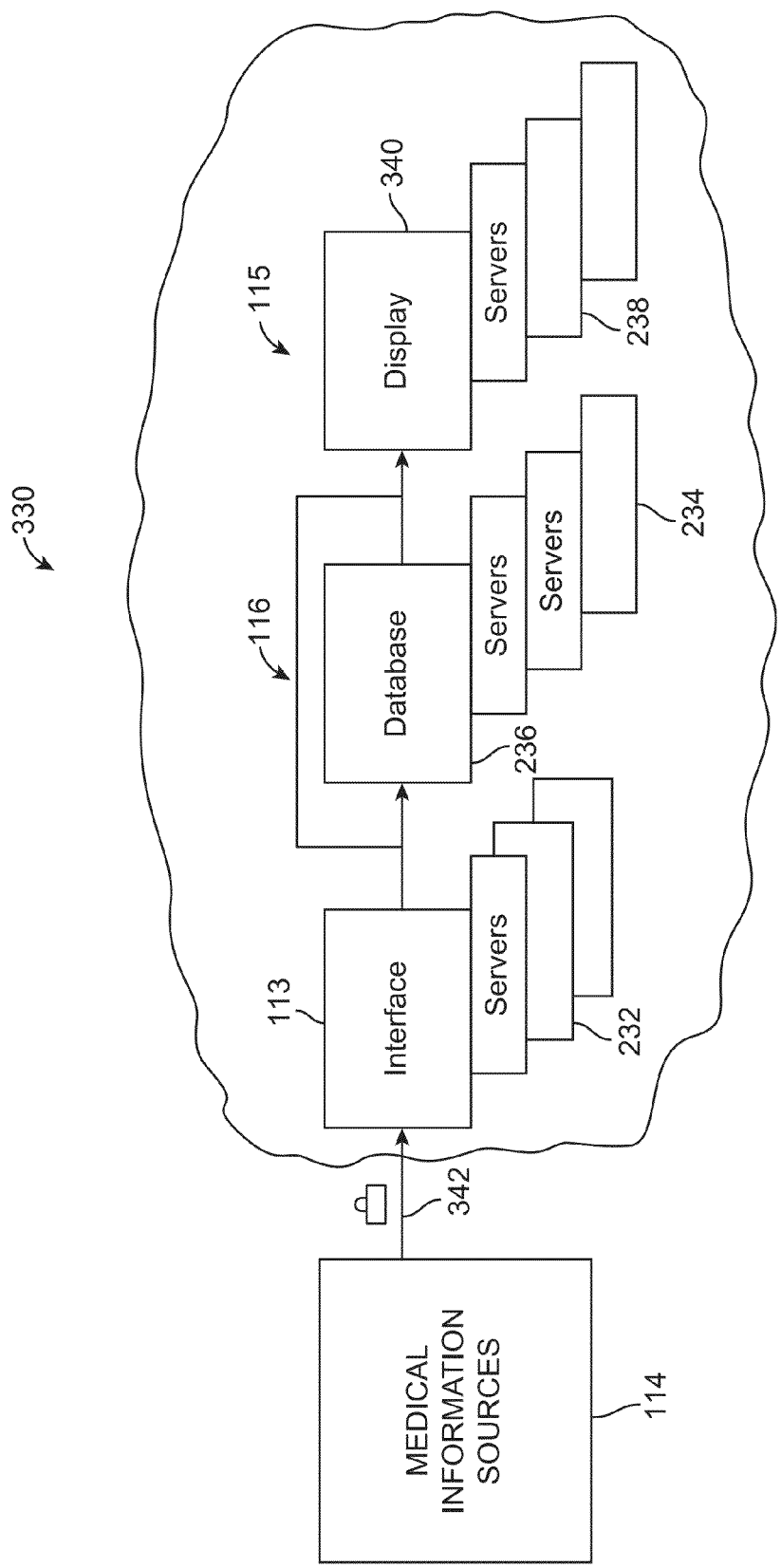
FIG. 3 shows an exemplary embodiment implementing the system using various devices, in accordance with some embodiments.

FIG. 3 shows an exemplary embodiment implementing the system 100 using various devices. That is, the medical system 330 is analogous to the system 100 and is shown to include the sources 114 coupled to communicate, securely, through the secure communication link 342, to the interface 113. The link 342 may be any suitable communication channel allowing information, of various formats and types, to be transferred to the interface 113 in a secure and encrypted fashion. Exemplary communication channels of which the link 342 is made include the Internet, VPN connections over the Internet, private dedicated digital lines such as T1, T3, E1, E3, SONET, and other fiber optic formats.

The interface 113, in some embodiments, is a software program that executes on one or more servers 232, which can be a server of any kind of suitable computing engine, such as personal computer (PC). The servers 232 receive secure information through the link 342 from the sources 114. The processor 116, in some embodiments, includes the module 236 and one or more servers 234, which may be any suitable computing engine, similar to the servers 232, including but not limited to PCs or servers.

The module 236 and servers 234 perform the tasks discussed above relative to the processor 116 and the display 340 and servers 238 perform the tasks discussed above relative to the processor 115 though these processors may and often perform additional tasks related to medical information, some examples of which are presented and discussed below and the rest of which are contemplated and achieve the various advantages, results and functions presented herein.

The processor 115, in some embodiments, includes display and visualization 340 executing on one or more servers 238, which may be any suitable computing engine, similar to the servers 232, including but not limited to PCs or servers. The display 340 is used to construct presentation and display information to users, such as the patient's records, billing information, and other types of medical information. The display 340, in some embodiments, also performs processing of some of the functions of the processor 115.

As shown in FIG. 3, the servers 232 are coupled to the module 236 and the servers 234, and to the display 340 and the servers 238 and the module 236 and servers 232 are coupled to the display 340 and the servers 238.

In some embodiments, the interface 113, servers 232, module 236, servers 234, display 340, and servers 238 are remotely located relative to the sources 114 and in some embodiments, remotely located relative to one another. Further, they are considered a part of the Internet cloud where, performing their tasks in a manner known as "cloud-computing". However, other manner of achieving the functions and advantages of the invention, including various other of implementation, not shown in FIG. 3 or other figures herein and/or not discussed are contemplated.

Figure 4:
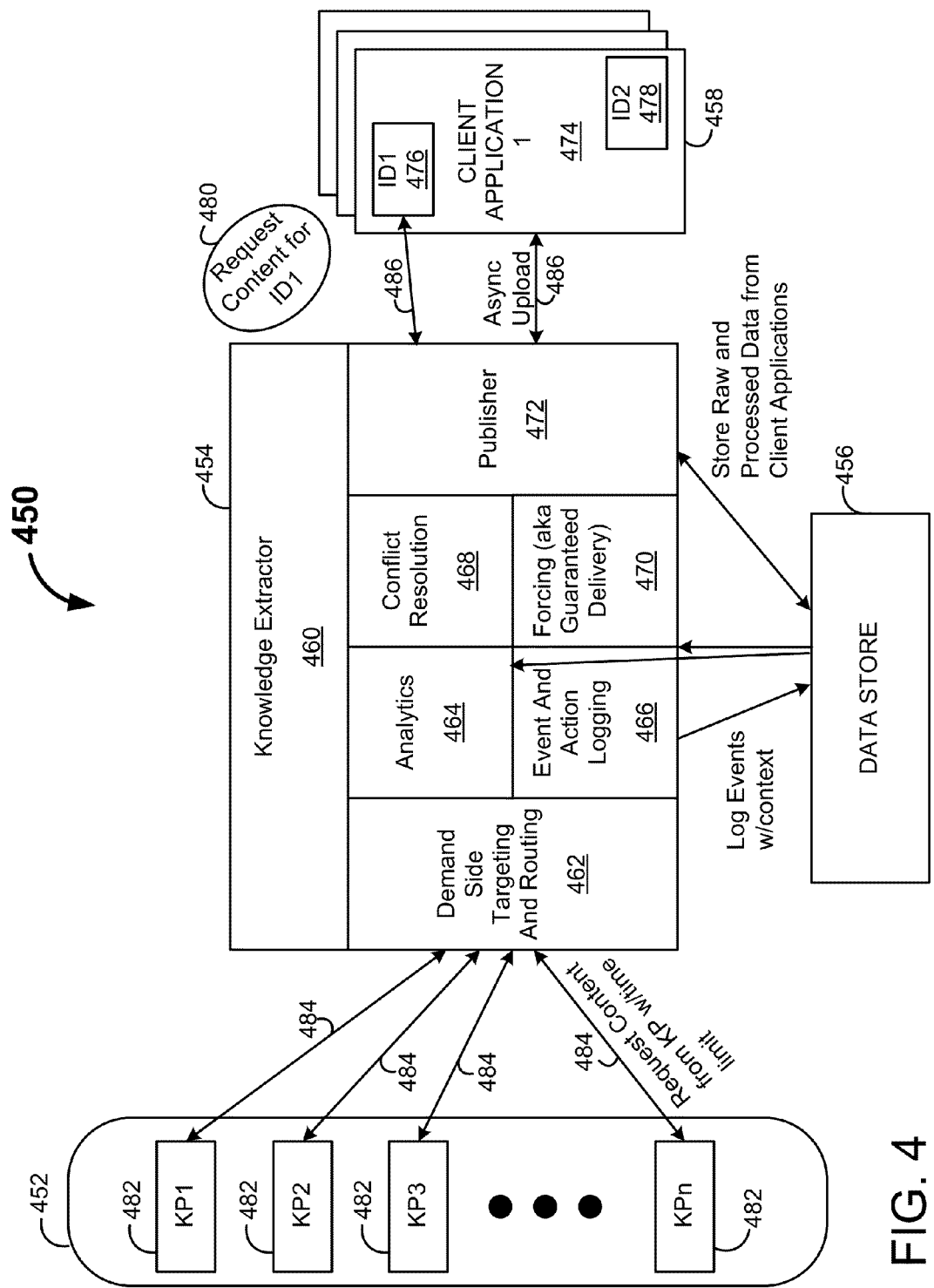
FIG. 4 shows a block diagram of a knowledge extraction system, in accordance with some embodiments.

FIG. 4 shows a block diagram of a knowledge extraction system 450, in accordance with an embodiment of the invention. Knowledge extraction may be employed by the agents in order to generate additional inferred events. The knowledge extraction system may be functionally separate from the MINE 112, or may be an integrated feature of the MINE 112, hosted by one of more of the processors 116.

The system 450 is shown to include a knowledge provider block 452, a knowledge extraction and exchange unit 454, a data store block 456, and a client application block 458. The block 458 executes client or user applications 474 using event streams generated by the knowledge extractor 460 (in addition to event streams generated by querying agents).

The block 452 is analogous to the sources 114 of FIG. 1 and is shown to include a number of knowledge providers 482, with each knowledge provider being analogous to one of the sources discussed above relative to the sources 114. The knowledge extraction and exchange unit 454 may include the back-end medical processor, shown in FIGS. 1 and 2. The knowledge extraction and exchange unit 454 is shown to include a demand-side targeting and routing block 462, an analytics block 464, an event and action logging block 466, a conflict resolution block 468, a forcing (or guaranteed delivery) block 470, a publisher block 472, and a knowledge extraction block 460. The block 458 is shown to include one or more impression domain (ID) blocks 476 and 478. While two ID blocks are shown in FIG. 4, it is understood that any number of ID blocks (e.g. problems, procedures, medications, allergies, "did you know?", patient safety items, billing enhancement items, and the like), as required by a user of the system 450, may be employed.

The knowledge extraction and exchange block 454 generally manages the overall process of delivering "content" to the ID blocks 476 and 478 in the form of event streams, including managing the data store block 456, managing interactions with the knowledge providers 482 and determining which results to present to the client application block 458 (which is generally analogous to the front end processor 115 of FIGS. 1 and 2) when a request of "content" is made by one of the ID blocks 476 and 478 and how to rank the requested results. An example of a request is shown at 480 in FIG. 4 where the block 476 is making the request. "Content", as used herein, refers to any information pertinent to the ID embodied as an event or event stream, for example a query string, image or hyperlink.

The data store block 456 is generally a storage device or a database storing raw and processed data received from the block 474, through the unit 454. Raw data is data that comes directly from the application 474. Processed data is data that has been processed or optimized for efficient use by knowledge providers. The knowledge extraction and exchange block 454 causes actions to be logged with context into the data store block 456 when data is being stored therein.

The knowledge extraction and exchange block 454 communicates with the client application block 458 bi-directionally and typically asynchronously such that when there is a change to the underlying data in the application of the block 458, such as an update to the patient chart, the block 458 sends this updated data to the publisher block 472. The client application block 458 is a client or user application with each of its ID blocks querying for and displaying its particular impression domain content. By way of example only, impression domain content includes items such as problems, procedures, medications, allergies, "did you know?", patient safety items, billing enhancement items, and so on. Each ID presents information to the user that is relevant to the specific patient/user/context at the time the information is displayed. For example, a patient safety ID would present a patient's past history of myocardial infarction to a primary care provider if that event were not noted as structured data the user's EHR application. The publisher block 472 receives content requests from the ID blocks 476 and 478 and in response returns content to be displayed in the blocks 476 and 478. Further, the block 472 receives actions (such as clicks) from the ID blocks 476 and 478, receives raw data (such as patient chart updates) from the application block 474, and manages storage of data in the data store block 456 (including action logs, raw client application data event streams, and data extracted for the specific needs of the knowledge providers 482 of the block 452).

The demand side targeting and routing block 462 routes content requests to the different knowledge providers 482, received from the client application block 458 by selecting a subset of knowledge providers in real time which it considers most relevant to the current patient/user/context based on criteria provided by the knowledge provider, such as "patient covered by Medicare Advantage", "user is a cardiologist", or "query includes the term EKG", and subsequently receives their responses, through the knowledge provider links 484. In some embodiments, if a knowledge provider 482 with an outstanding content request does not respond within a prescribed amount of time, the request is cancelled.

The conflict resolution block 468 receives content from the demand side targeting and routing block 462 and advantageously determines which of the responses from the knowledge providers 482 to pass to the forcing block 470 and in which rank order. The conflict resolution block 468 uses the content from the ID block 476 or 478 (e.g., patient, user, query) along with analytics on the performance of past knowledge provider results to determine which results are most likely to be useful. For example, if an endocrinologist user always clicks on the hemoglobin a1c history after performing a diabetes search, the ID for labs may start automatically displaying the history in response to a diabetes context for that particular user. If enough endocrinologists perform the same action, the ID for labs may start automatically displaying the history for all endocrinologists, whereas such an automatic action might not be performed for general practice users searching for the same diabetic context.

The forcing block 470 receives ranked and selected results from the conflict resolution block 468 and further determines to potentially override the ranking determined by the conflict resolution block 468. For example, if only one result can be displayed in a particular ID block, and it receives a high-value reimbursement result and an important patient safety result, the patient safety result might be given priority over the reimbursement result.

The event and action logging block 466 stores action data, such as click-through actions in the data store block 456, along with context information (ID context, date, time). Action data refers to end user actions, e.g., clicking on a particular content that is displayed for more information or history.

The analytics block 464 computes summary statistics for events and actions and places them in the data store block 456 for use by the conflict block 468. End user statistics like click-through rates and dwell times may also be computed by the analytics block 464.

Each of the ID blocks 476 and 478 sends a request to the knowledge extraction and exchange unit 454 asking for certain kinds of result (text, images, links, diagnosis codes) from the knowledge extraction and exchange unit 454. A typical request includes the number of results desired and the context of the request, such as patient identifier, user identifier (and user role, such as specialty, physician or coder or medical assistant, etc.) and the search query. The ID block 476 or 478 is responsible for determining how the results are presented to the user of the system 450. For example, when an action is taken, such as a click on a search link, the ID block 476 or 478 also submits this information to the action logging block 466.

Each of the knowledge providers 482 computes and returns results that are relevant to a particular ID block request. In some embodiments, the knowledge providers 482 have access to the data store block 456. For example, a knowledge provider might return PubMed articles, up-to-date articles, or best treatment practices that are relevant to the patient/user/context.

II. Knowledge Extraction Processes

Figure 5:
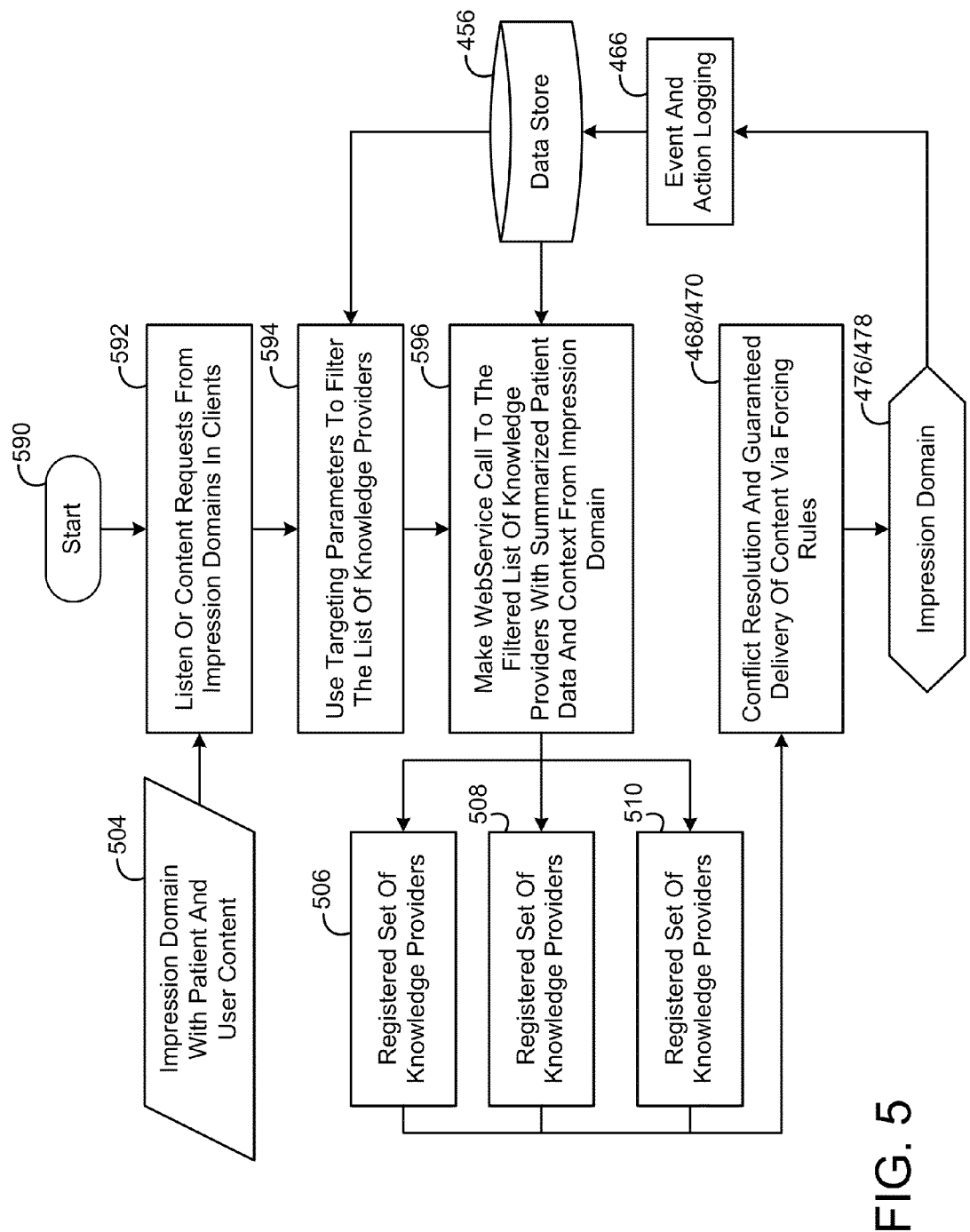
FIG. 5 shows a flow chart of some of the steps performed by the unit 454 of FIG. 4, in conjunction with some of the blocks of FIG. 4 and in accordance with a method of the invention.

FIG. 5 shows a flow chart of some of the steps performed by the knowledge extraction and exchange unit 454 of FIG. 4, in conjunction with some of the blocks of FIG. 4 and in accordance with a method of the invention. The method starts at 590 and at step 592, content requests from the blocks 476 and 478 are awaited by the unit 454. In the meanwhile, at 504, the blocks 476 or 478 may provide the unit 454 with patient and/or user "content" and when they do, the process proceeds to step 594 where targeted parameters are used to narrow the list of knowledge providers 482 in real time based criteria provided by the knowledge provider, such as patient is covered by Medicare Advantage, user is a cardiologist or query includes the term "EKG". Targeted parameters may be received from the block 456, which also provides information for the next step 596. A narrowed list of knowledge providers is referred to herein as "registered set of knowledge providers". At step 596, the knowledge extraction and exchange block 454 makes webservices calls to the narrowed (or "filtered") list of knowledge providers with a summarized patient data and context from the blocks 476 or 478 obtained by knowledge extraction block 460. The summarized patient data is then passed on to the narrowed (or "filtered") list of knowledge providers blocks 506-510. The narrowed (or "filtered") list of knowledge providers 506-510 provide clinically-relevant knowledge to the blocks 468 and 470 where conflict resolution is performed and delivery of content is guaranteed via forcing rules. "Forcing rules" refer to a set of rules that may override decisions made by the conflict resolution module 468.

The outcome of the blocks 468 and 470 is then provided to the block 476 or the block 478, which subsequently captures events and actions and transmits them to the block 466. These events and/or actions are stored, in their raw form, in the block 456.

Figure 6:
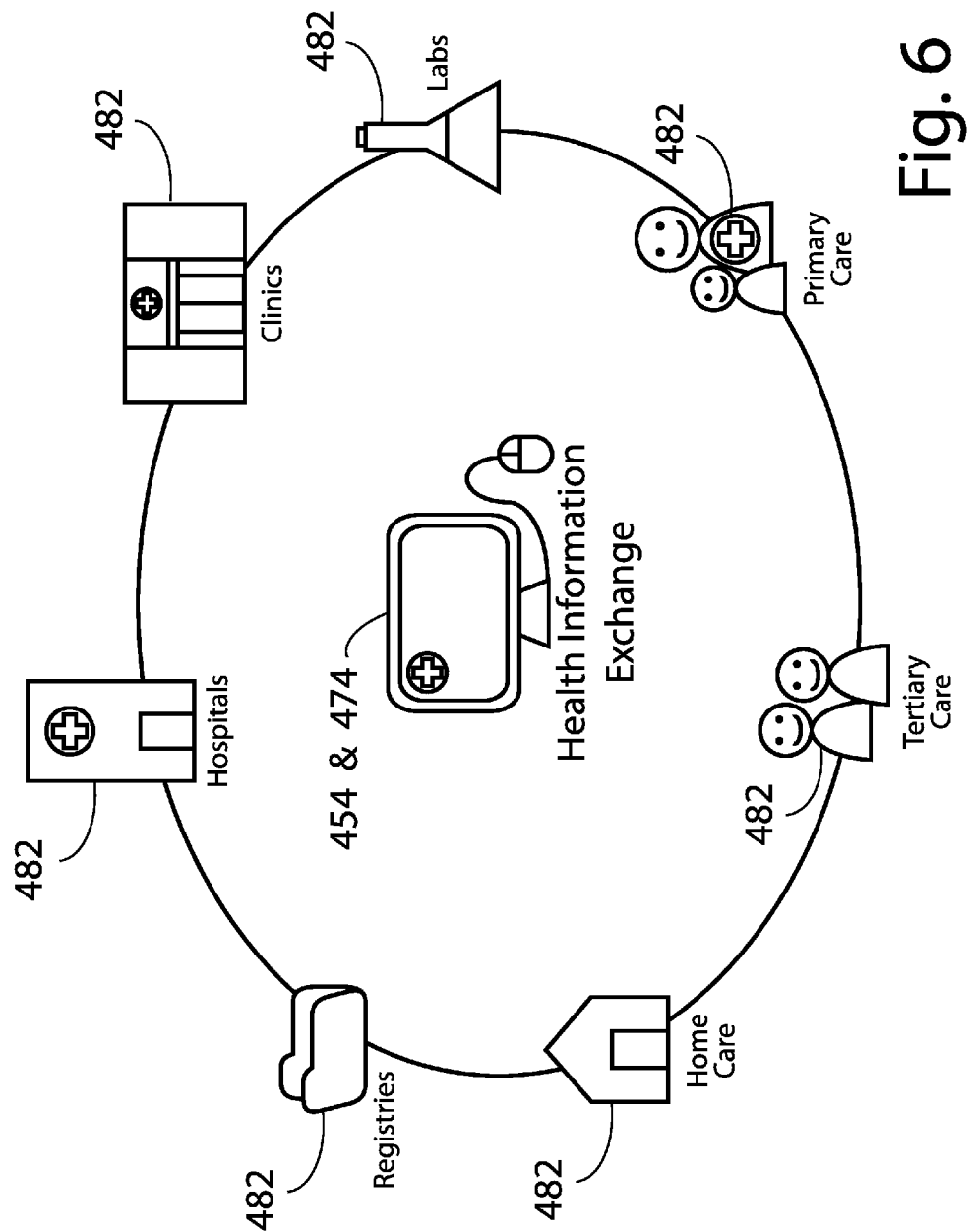
FIG. 6 shows an example of the knowledge extraction and exchange unit 454 and the client application 474 and examples of knowledge providers 482.

FIG. 6 shows an example of the knowledge extraction and exchange unit 454 and the client application 474 and examples of knowledge providers 482. In FIG. 6, the knowledge extraction and exchange unit 454 and the client application 474 are shown to be a mobile device and/or tablet, and the knowledge providers 482 are shown to be a home care facility, a tertiary care facility, a primary care, labs, clinics, hospitals, and registries. It is understood that the knowledge providers 482 of FIG. 6 are merely examples of knowledge providers, in fact, the knowledge providers 482 as well as the knowledge extraction and exchange unit 454 and the client application 474 can be in a field other than the medical field, such as legal services, among others that are contemplated.

III. Big Data Usage

The subsequent figures and accompanying text illustrate downstream applications that can capitalize upon the big data platform being generated from the event streams. These downstream processes and application may provide increased revenue to a healthcare organization, increase care quality, and provide other value added outcomes.

Figure 7:
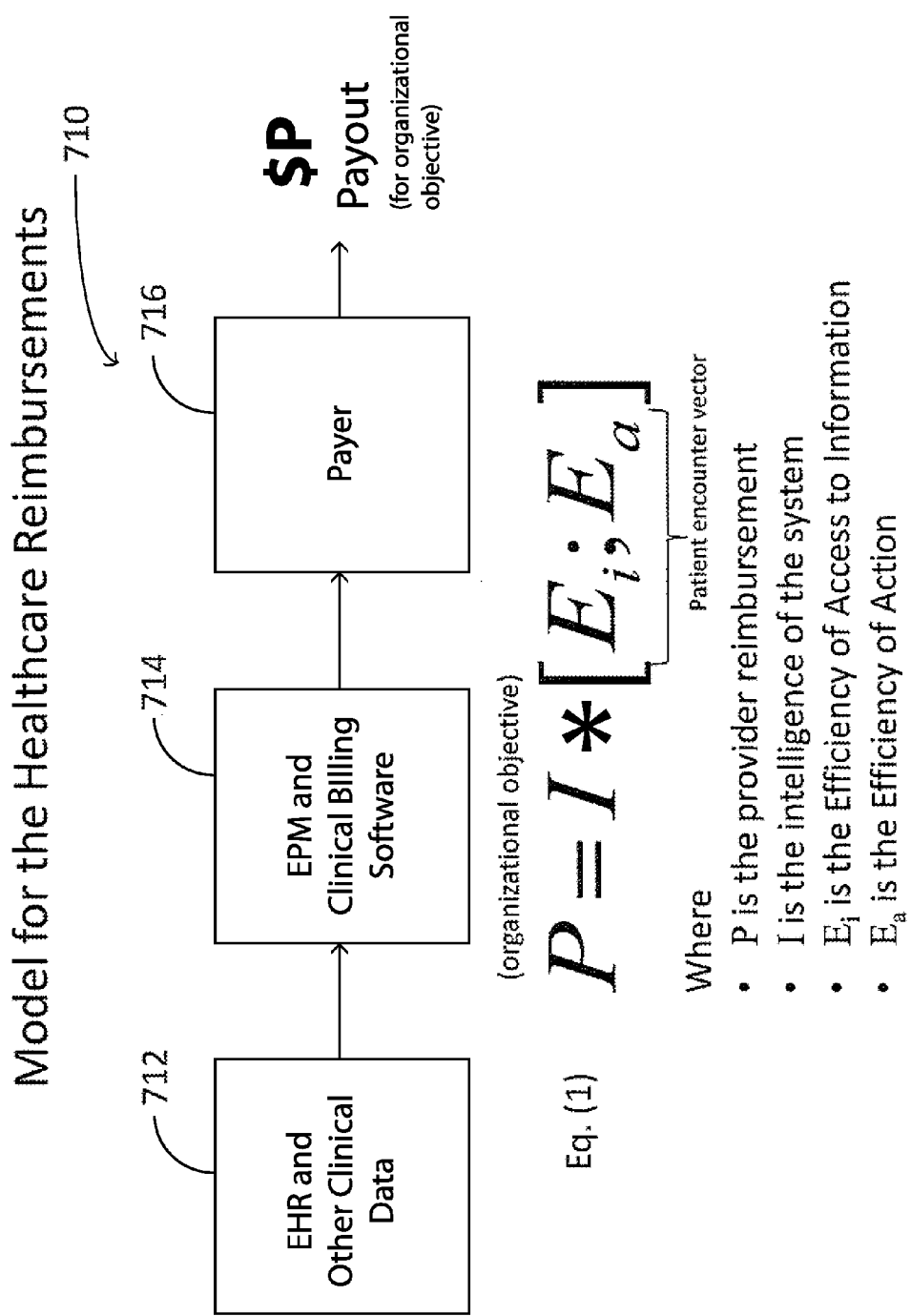
FIGS. 7 and 8 show a model of a healthcare reimbursement system, in accordance with a method and embodiment of the invention.
Figure 8:
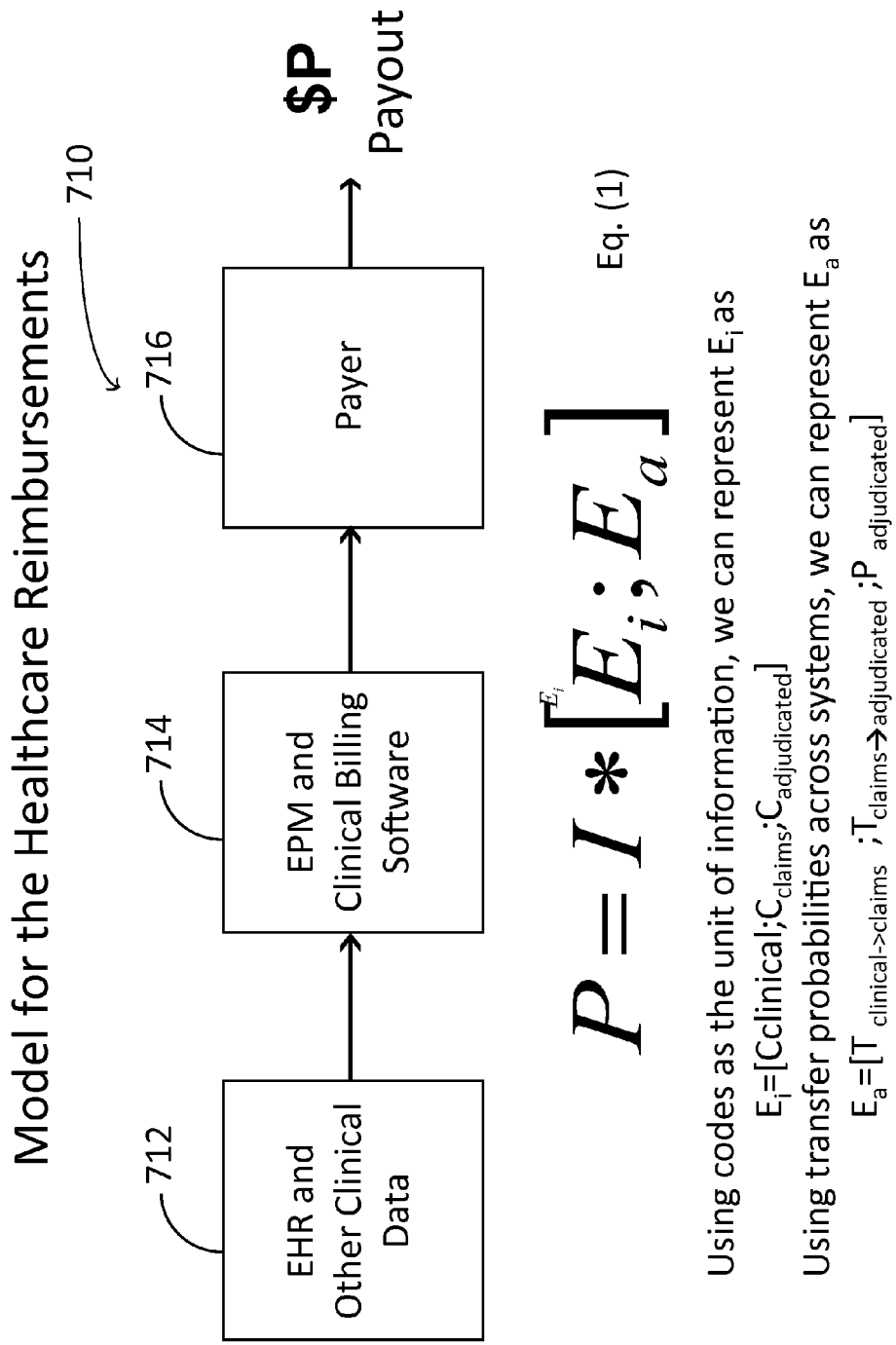

FIGS. 7 and 8 show a model of a healthcare reimbursement system, in accordance with a method and embodiment of the invention. In each figure, Eq. (1) is shown to represent the relationship between the organizational objective (P) and efficiency (I) and patient encounter vector $[E_i; E_a]$. In Eq. (I), the symbol "*" represents a multiplication operator, the symbols "[ ]" represent a matrix and the symbol ";" represents concatenation. The system prompts for actions that move data from one place to another to achieve the organizational objectives (P).

Figure 9:
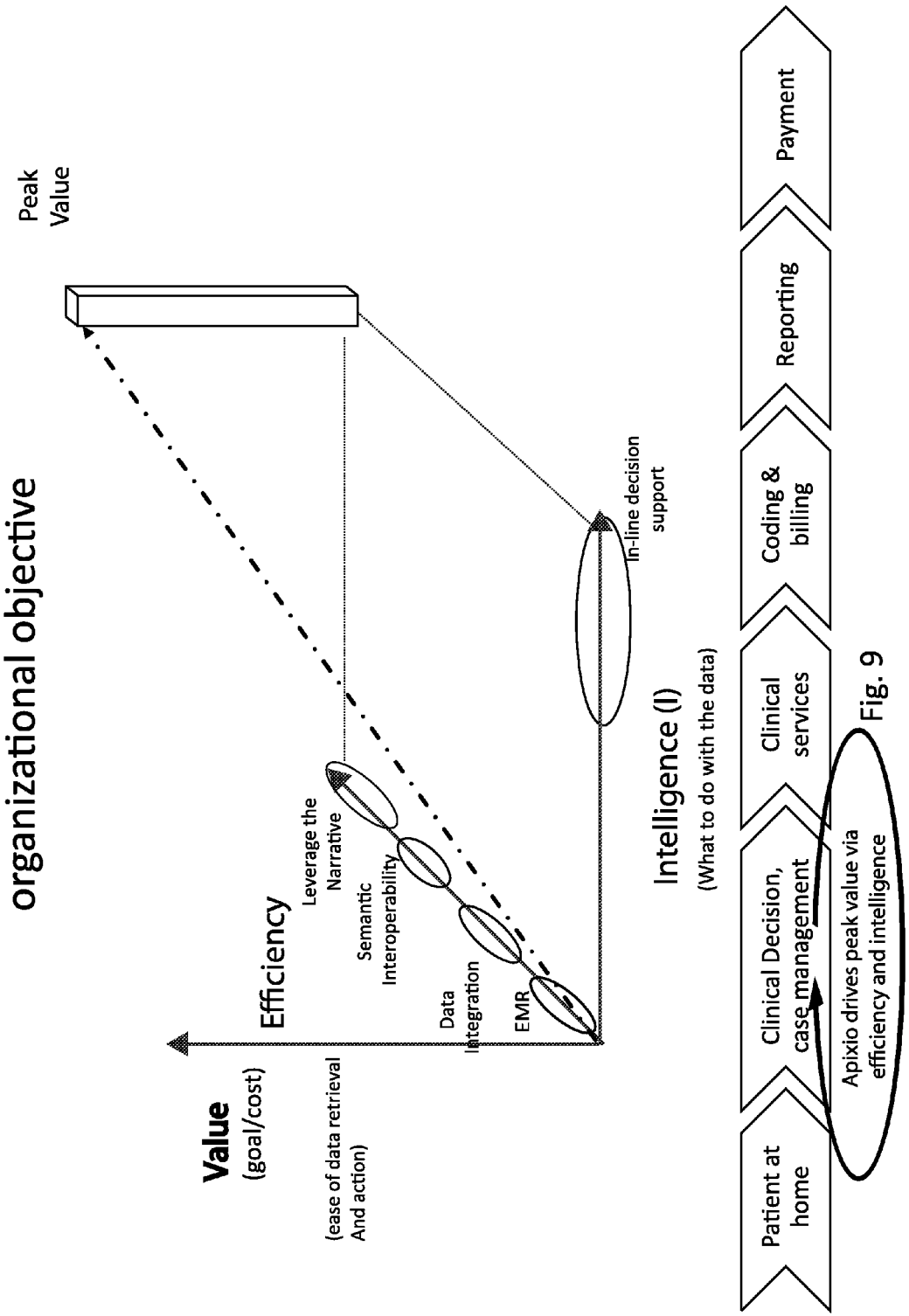
Figure 11:
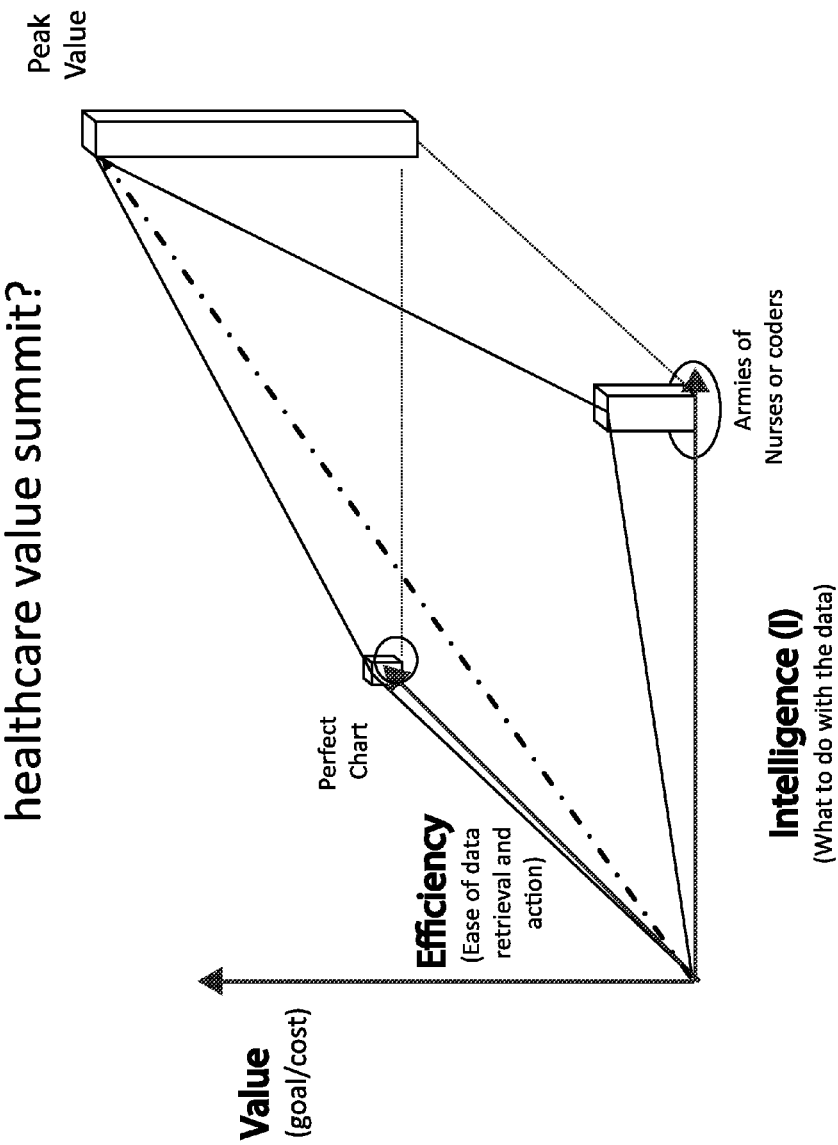
Figure 12:
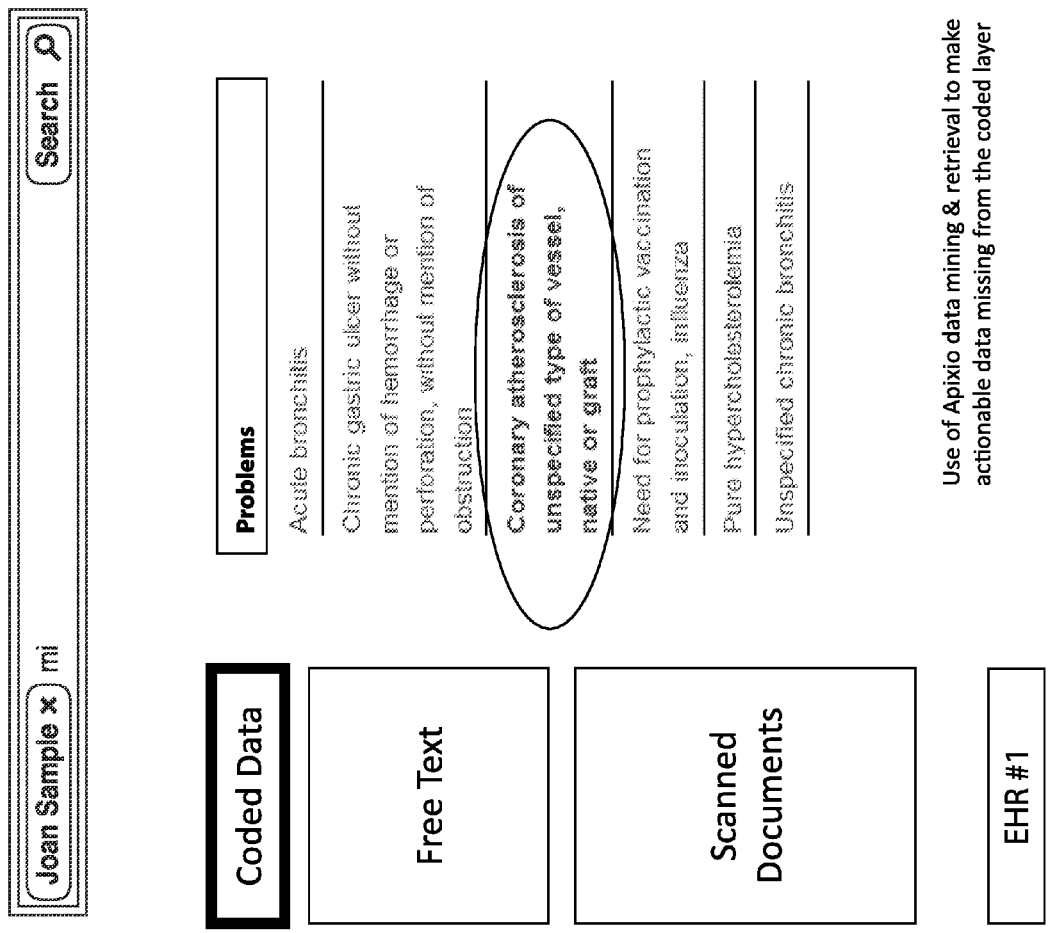
Figure 13:
Figure 15:
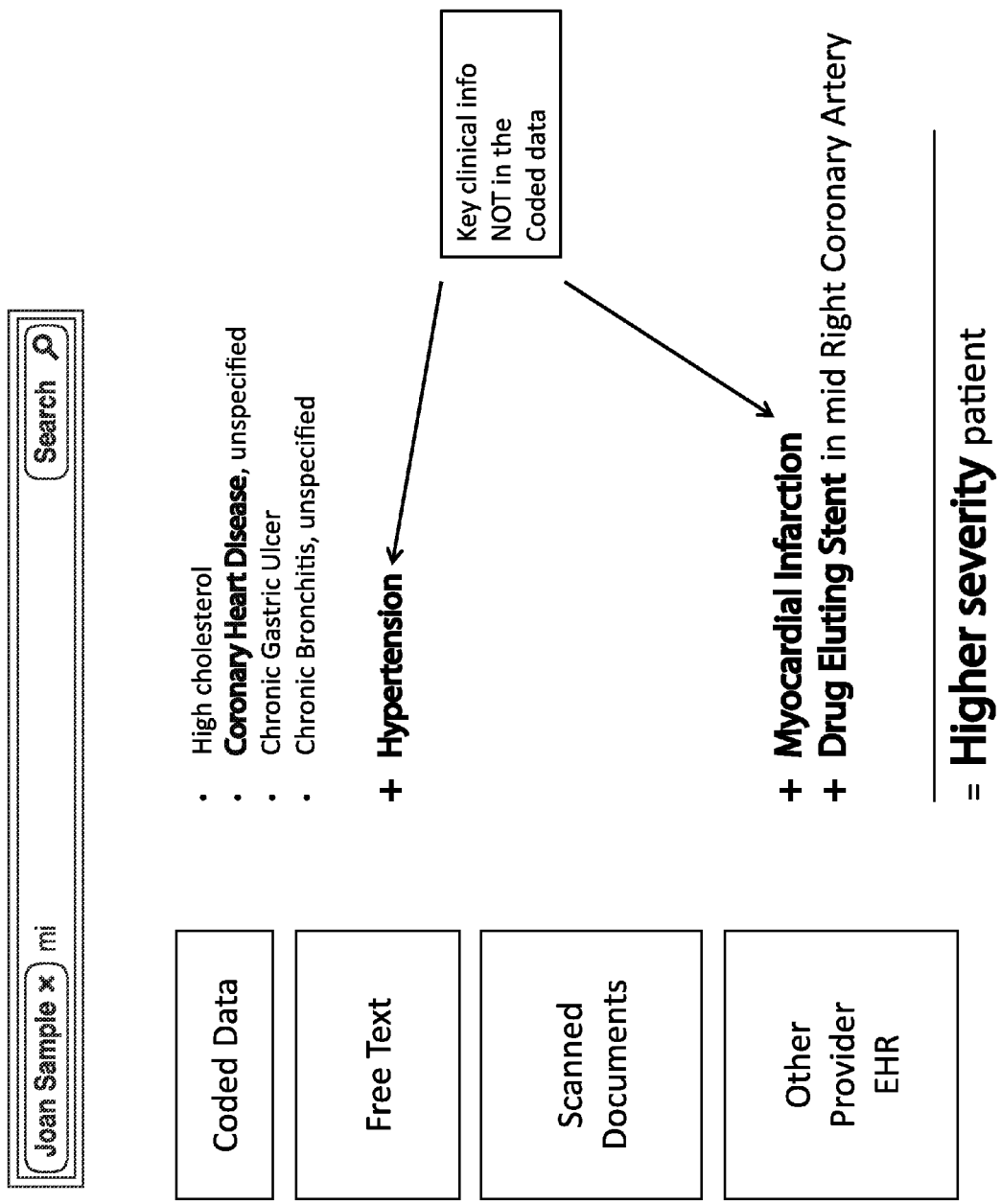
Figure 16:
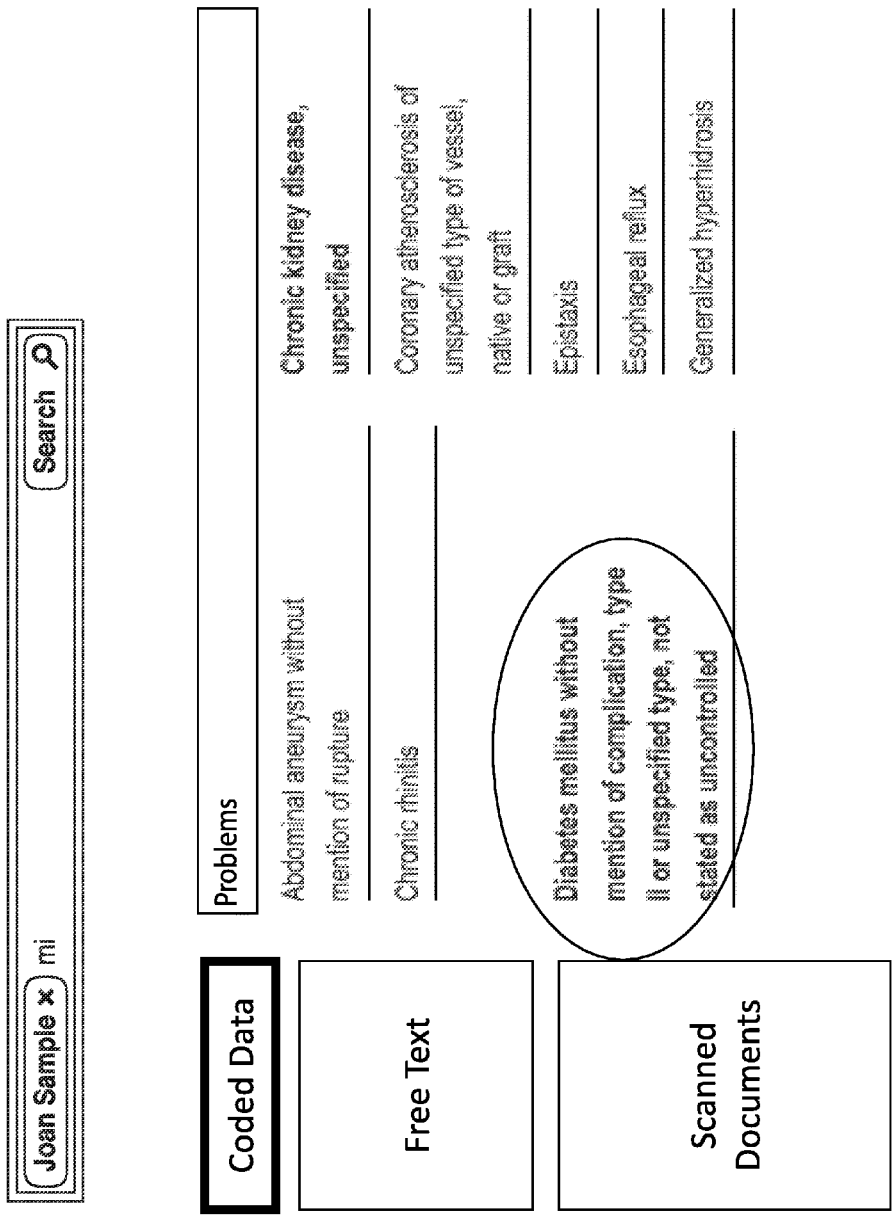
Figure 17:
Figure 18:
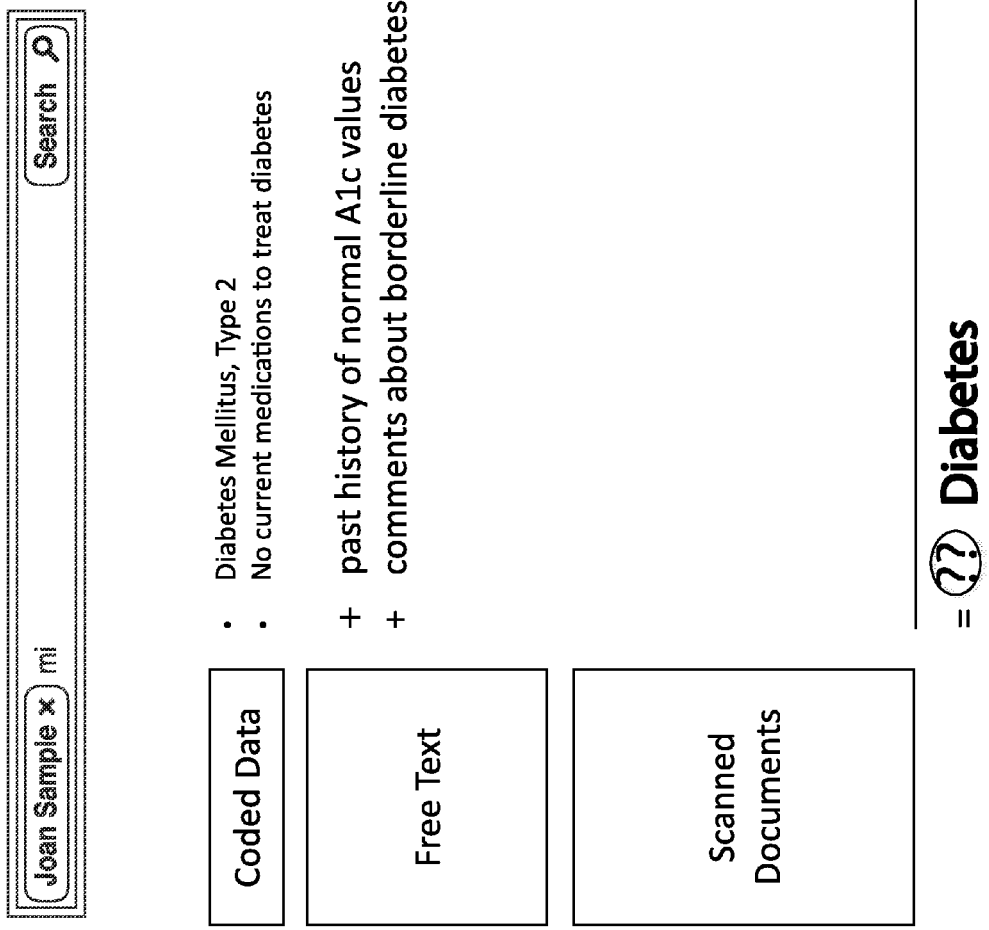

FIGS. 9-11 each show a graph of the intelligence, shown in the x-direction, versus value, shown in the y-direction, of various performance improvements realized using the various methods and embodiments of the invention.

FIGS. 12-18 show an example of a patient/user, Joan Sample, benefiting from the process of extracted information used to determine potential conditions, in accordance with a method of the invention. Of note, coded information in medical records typically includes only 10-20% of total information. The remaining data is in textual form, or even in the form of scanned documents. By reducing this information to events, and compiled event streams, the data available for analytics by applications is expanded dramatically.

Figure 19:
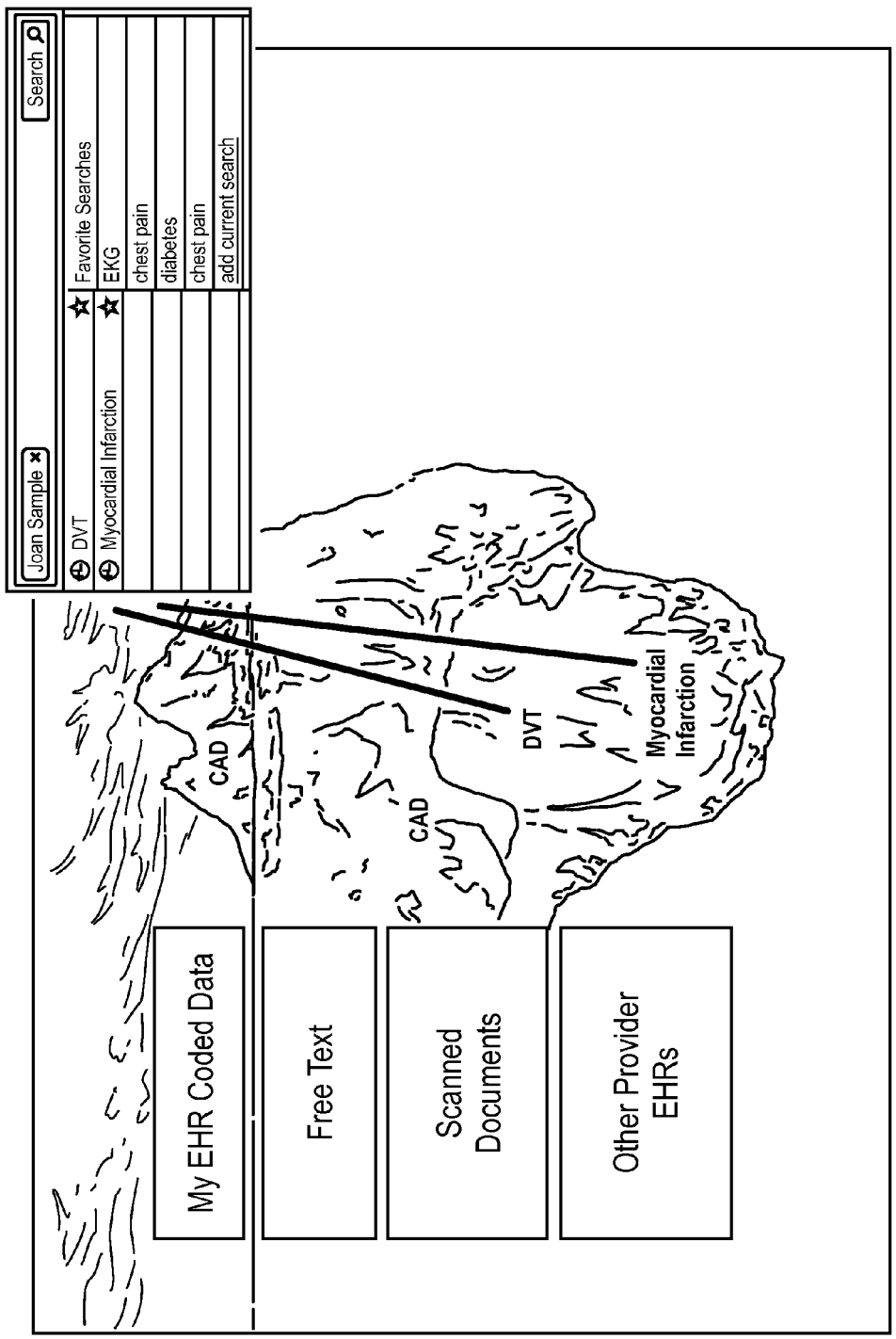
FIG. 19 shows MI and DVT extracted from otherwise hidden information, other provider EHRs and scanned documents, by using the knowledge-based extraction methods and embodiments of the invention.

FIG. 19 shows MI and DVT extracted from otherwise hidden information, other provider EHRs and scanned documents, by using the knowledge-based extraction methods and embodiments of the invention.

Figure 20:
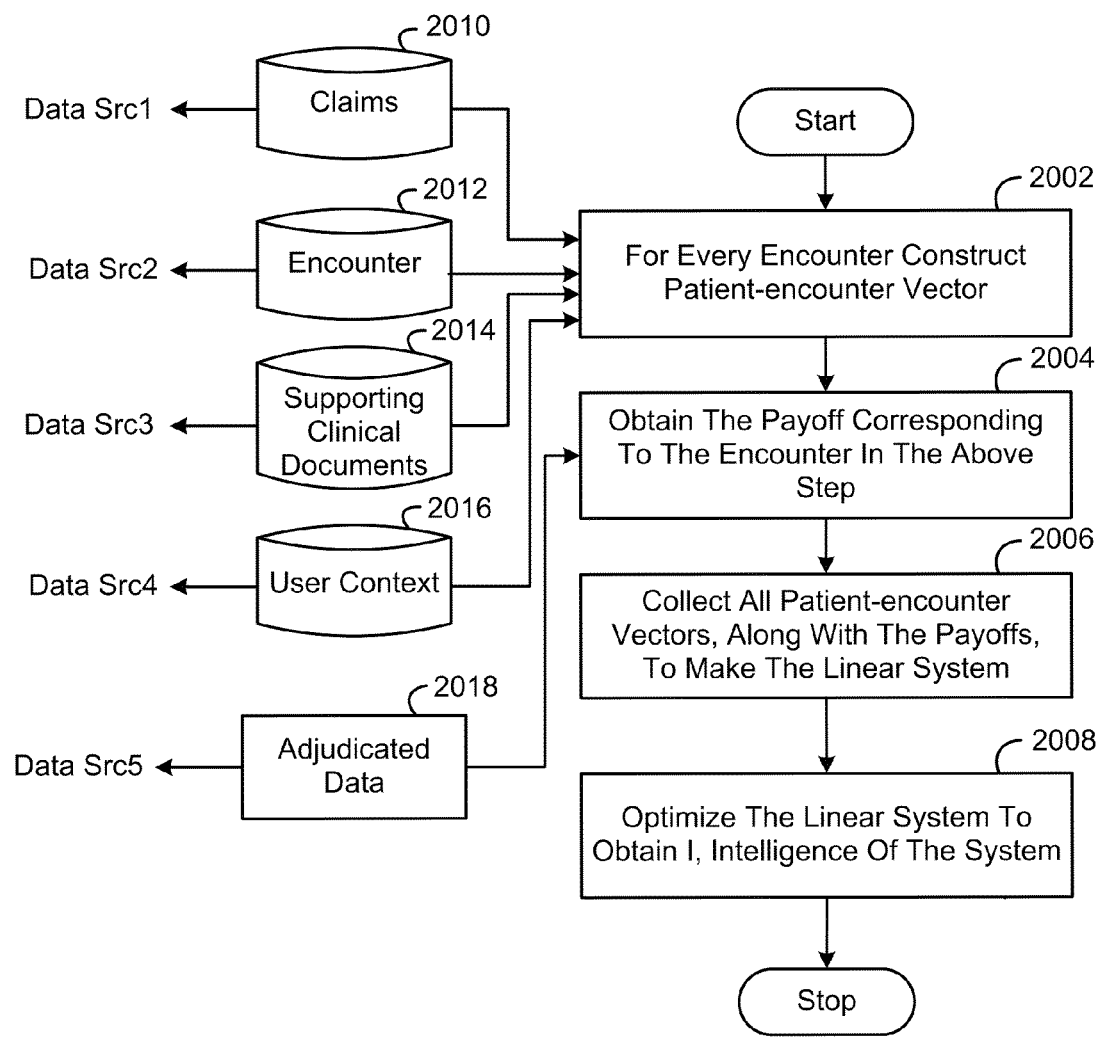
FIG. 20 shows a flow chart of the steps for determining the intelligence (I) of a healthcare system, in accordance with a method of the invention.

Other downstream applications may include determining an intelligence value for a healthcare system. Intelligence may be utilized in the determination of care quality, and means for improving the quality. FIG. 20 shows a flow chart of the steps for determining the intelligence (I) of a healthcare system, in accordance with a method of the invention. In this example process, claims 2010, encounters 2012, clinical documents 2014, and user context 2016, are all utilized by the processor to construct a patient-encounter vector (at 2002). This vector and adjudicated data 2018 are used to obtain the payoff corresponding to the encounter (at 2004). All patient encounter vectors and all payoffs are collected to make a linear system (at 2006), which may be optimized to obtain the intelligence of the system (at 2008).

Figure 21:
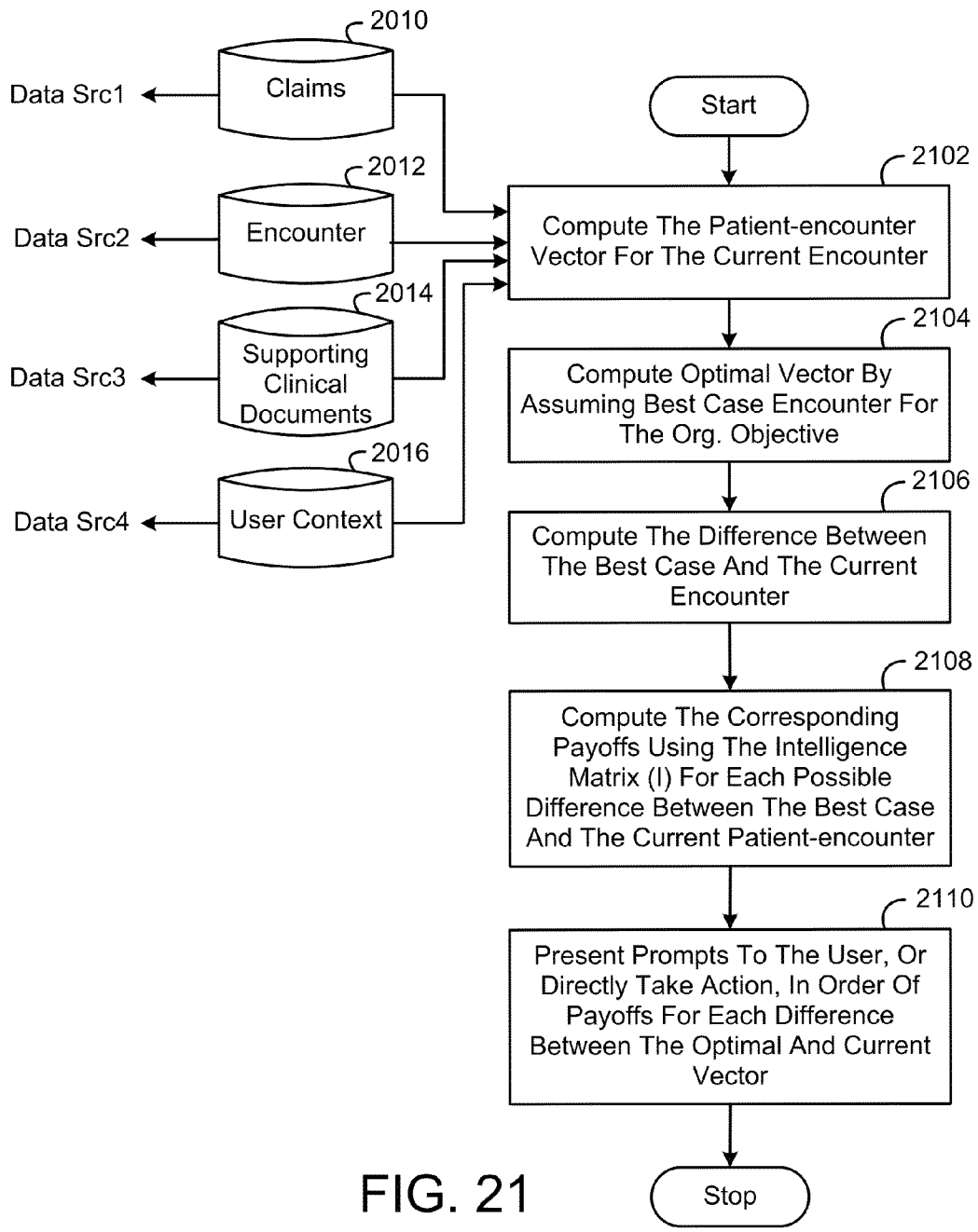
FIG. 21 shows a flow chart of the steps for application of hierarchal condition categories (HCC), in accordance with a method of the invention.

Likewise, FIG. 21 uses the intelligence generated in the manner of FIG. 20, in conjunction with encounter vectors to optimize encounters. In this example process, the data "src" or sources shown on the left side of the page are data that is provided by various sources, such as claims 2010, encounters 2012, clinical documents 2014, and user context 2016.

The steps of FIG. 21 are for application of hierarchal condition categories (HCC) and advantageously identify the first order HCC gap alerts. The patient-encounter vectors are computed, or recalled if previously calculated (at 2102), and an optimal vector is likewise computed under a "best case encounter" according to the organizations objectives (at 2104).

The difference between the best case vector and the actual encounter vector is then computed (at 2106). The corresponding payoffs for these differences are then computed (at 2108) using the intelligences previously calculated. This payoff information is value lost to the organization due to non-optimization of encounters. As such, prompts may be presented to the user, or direct action may be taken, in the order of the payoffs in order to rectify the lost opportunity (at 2110).

Of course, other downstream applications are considered within the scope of this disclosure. For example, beyond hierarchal condition category optimization, other applications may be employed to optimize quality of care, analyze populations, manage protocols and treatments, and perform predictive analytics, manage customer relationships, and other such downstream applications. It should be noted that this listing is not exhaustive, and any applicable downstream application may be employed as desired for system operation and utility.

IV. Event Stream Platform

Figure 22:
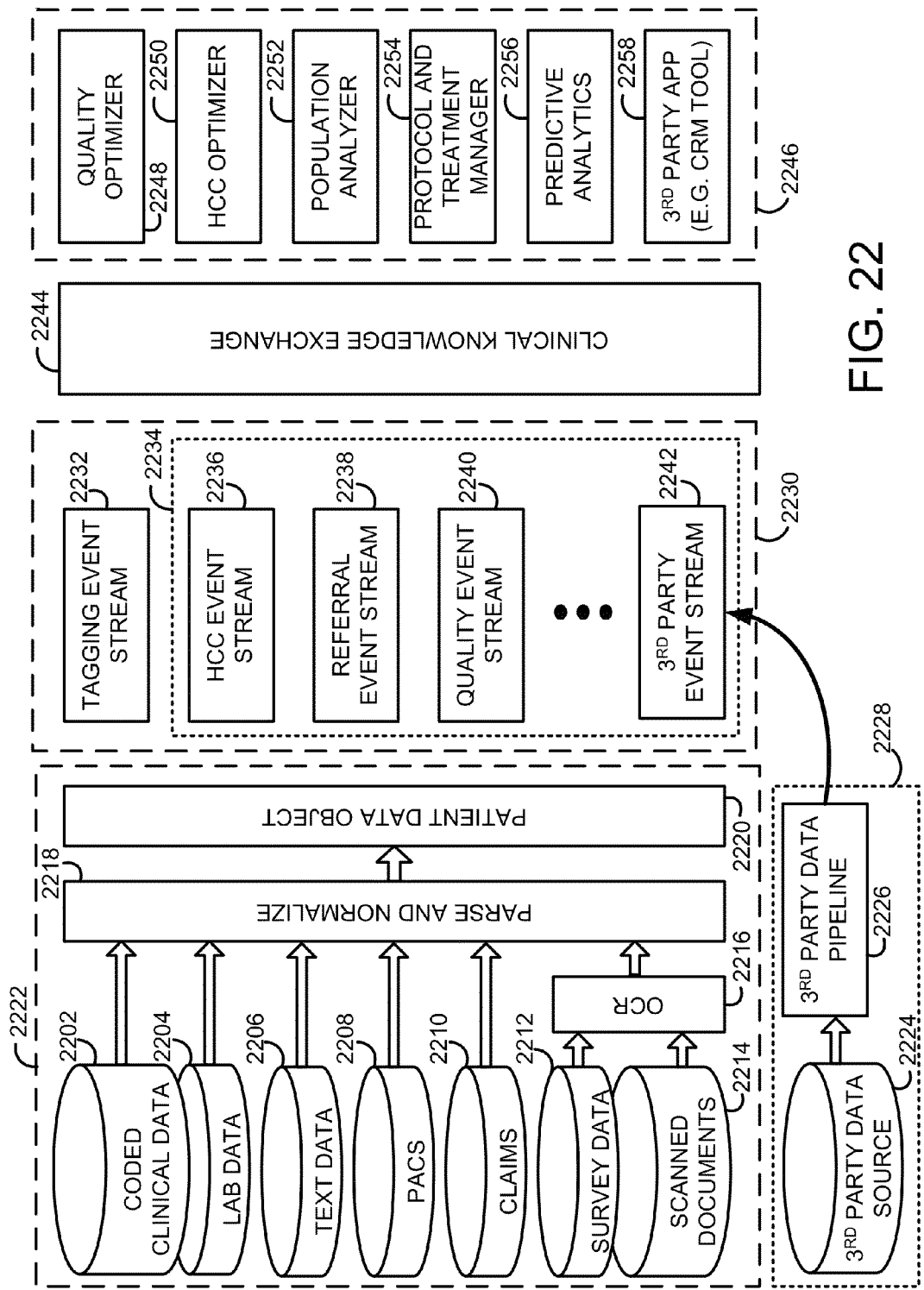
FIG. 22 shows a data flow diagram illustrating event stream generation and usage, in accordance with some embodiments.

Attention shall now be focused upon the processes and data management within the medical system 100 for the generation of an event stream platform that enables bid data analytics. Referring to FIG. 22, a data flow diagram is provided which illustrates how raw medical information is handled, managed and manipulated in a manner to enable consumption by applications.

In this figure, a comprehensive set of data sources are displayed. These include coded clinical data 2202, lab data 2204, textual data 2206, PACS 2208, claims 2210, survey data 2212 and scanned documents 2214. All these data sources are available internally within a healthcare organization. These data sources may be the same or similar to those illustrated at FIGS. 1 and 2 at part number 114, and part 452 of FIG. 4.

The survey data 2212 and scanned documents 2214 are not in machine readable form and must be converted by optical character recognition (OCR) to a format that may be utilized by the computer system. All the raw data (including OCR data where appropriate) are parsed and normalized by a module 2218. This normalized data is then indexed, by an indexing module, as seen in FIG. 2 at part 234, to generate a patient data object 2220. The patient data object 2220 may be stored in a data store, such as that shown at part 456 of FIG. 4. The entire data flow from raw data sources, to OCR as applicable, parsing and normalization, and indexing into a patient data object is referred to as a data aggregation pipeline 2222.

In addition to the internal data aggregation pipeline 2222, a third party data source 2224 may be similarly prepared via a third party data pipeline 2226, within the confines of the third party system 2228.

The resulting patient data object 2220, and third party data object from the third party data pipeline 2226 may be provided to a big data index pathway 2230 which is a function of the knowledge extractor 460 of FIG. 4. The patient data object 2220 may undergo meta tagging by the tagging module at 2232. The tagging module is a part of the module 234 which is included in the processor 116 of FIG. 2. From the tagging, an initial event stream is generated.

As previously discussed, "events", as used in this application, are defined as facts (something that is true or false) that has occurred in a specific time for a specific subject (in the clinical context, it could be the patient, an organization, etc.), attributed to a specific agent (i.e. a cause—could be a provider, organizations, etc., or a some combination of them), a source (original source of where that fact originated from), and an episode grouping (typically an encounter in the clinical context). An event can also be associated with a collection of named values. An "event stream" is a collection, or set, of events.

In order to provide more clarity into the form of an event, an example is provided below. In this example a patient, John Sample, has undergone a medical examination on Nov. 26, 2011 which generates a medical record. A portion of this example medical record, including the physician impression and notes, is provided:

Impression:

The patient is a 68-year-old gentleman admitted for:
1. Pneumonia, chest x-ray confirms the same with shortness of breath.
2. Ischemic cardiomyopathy with abnormal stress test, inferior defect, ejection fraction 30% with elevated BNP, possibly secondary to underlying infection versus decompensated congestive heart failure.

The medical system is capable of parsing, normalizing, indexing and tagging this medical information into an event with the following structure:

<Patient John Sample, "depressed contractility", GPRO2012:HF_LVSD_CODE, 11/26/2011, 11/26, 2011, Outpatient Encounter on 11/26/2011, Document Titled "Ea-Cardiology Consolut" dated 11/27/2011 authored by chris cardiologist, Inferred Event from Document, "EF:30%", " . . . calculated ejection fraction of 30% with . . . ", ClinicalEvent, 11/26/2011, End-of-Time>

In this event, a number of values are recorded, these include:

1) The Subject, which is a required element of the event. In this example, the subject is "Patient John Sample".
2) The Evidence Used to Infer the Event. In this example the evidence is the term "depressed contractility" in the physician's impressions; however the evidence may include any of a collection of terms, output of a machine learning model, etc.
3) The Fact that was inferred from the evidence. This too is a required element of the event. Here a code is the Fact being inferred.
4) A Start Date of the event is also required. In this case, the start date is the date of the medical examination.
5) Likewise, an End Date of the event is required. In this case, the end date is the date of the medical examination.
6) An episode level Grouping may also be provided in the event as an element. Some analytical tasks require an episode level grouping. In this example, the grouping is an "outpatient encounter" on the specified date. Other episode groupings could include a multilevel grouping such as inpatient stay in a hospital with multiple episodes of care, etc.
7) The source of the event is also required for review and auditing purposes, and thus is typically included as an element of the event. Here the source is the example physician generated document. Sources can include any of those illustrated above in relation to FIG. 22.
8) The type of event is also required for audit, review and feedback loop based improvement of algorithms. In this example, the type of event is an inference from a document. Other event types could include continuity of care events such as referrals, administrative events like utilization management, revenue cycle events such as payments and other financial transactions, etc.
9) Named values may also be a component of the event. Named values are attributes with names and corresponding values. In this example, the attribute name is "ejection fraction" whose value is "30%."
10) A Snippet of the source may also be provided in the event. The snippet may be important for review and feedback loop based improvements. In this example "snippet goes here" was utilized for the sake of clarity. However, in an event such as this the snippet may include text such as: "Nuclear myocardial perfusion scan with adenosine in the office shows depressed contractility with inferior reversible defect. Ejection fraction is 30%."
11) The event classification is the next element of the event. Here the event classification is "ClinicalEvent". Other event classifications could include Administrative events, Eligibility events, Billing events, Audit Events and others. In some embodiments, the event classification and event types my be combined into a single field.
12) Lastly, Expiry Information is provided as a date range (validAfter, validBefore). The Expiry Information indicates what time periods the event is good for. In this example, the event starts as of the clinical diagnosis date, and extends into the future indefinitely. Other events may have expiration dates, such as "current eligibility within an insurance plan."

A set of events is an event stream. Once tagged at 2232, the event stream is provided to one or more agents 2234 for inference of other events and the generation of expanded event streams. An "agent", as used in the context of this application, is any process that consumes an event stream, along with other external sources of knowledge (such as dictionaries, machine learning models, etc.) and creates new inferred events that are added to the original event stream. Agents perform these inferences using knowledge extraction, as disclosed in detail previously, and first order logical queries.

For example, an HCC agent could consume the initial event stream and generate an HCC event stream 2236. This HCC event stream could be consumed by a referral agent to develop a referral event stream 2238. The referral event stream 2238 would include all the events of the HCC event stream 2236 in addition to the newly inferred events generated by the referral agent. Other agents may include a quality agent, third party agents, and the like, each capable of generating a corresponding quality and third party event stream 2240 and 2242, respectively.

In some embodiments, each agent may iteratively process the event streams; thus the quality agent may process the initial event stream to generate a quality event stream which may be then processed by the third party agent to generate a third party event stream. The quality agent may then consume the third party event stream (iterative functionality) to generate a new quality event stream that is further expanded by new inferences based upon events generated by the third party agent. Clearly, as the number of agents increases the number of iterations increases exponentially. This results in very rich event streams.

Eventually, despite repeated iteration, no new inferences are able to be generated. In some embodiments, the final event stream might be projected by transformations including, but not limited to, "rolling up" (grouping and aggregating, for example by or to a node within a knowledge graph), filtering, et cetera, before sending it to a clinical knowledge exchange. This final event stream is then provided to the clinical knowledge exchange 2244 for distribution to downstream applications. The clinical knowledge exchange 2244 includes the presentation and quality checking modules 230 and the querying servers 232 of FIG. 2. The clinical knowledge exchange 2244 enables the consumption of event streams by applications 2246. Some applications considered by this application include a quality optimizer 2248, an HCC optimizer 2250 (discussed previously), a population analyzer 2252, a protocol and treatment manager 2254, predictive analytics 2256, and other third party applications 2258. In some embodiments, the downstream applications may be a combination of internal applications and external third party applications. In some embodiments, applications may be patient independent, patient specific and population specific.

Further, the generation of an event stream and the clinical knowledge exchange allows for third parties to configure customized document processing pipelines, map the output format of event streams via the third party applications, and publish and index events streams in a consolidated platform. The applications that these third parties develop are then able to consume their configured event streams. The platform, via the clinical knowledge exchange, may provide authentication and access controls for the applications in order for them to work with multiple event streams.

Figure 23:
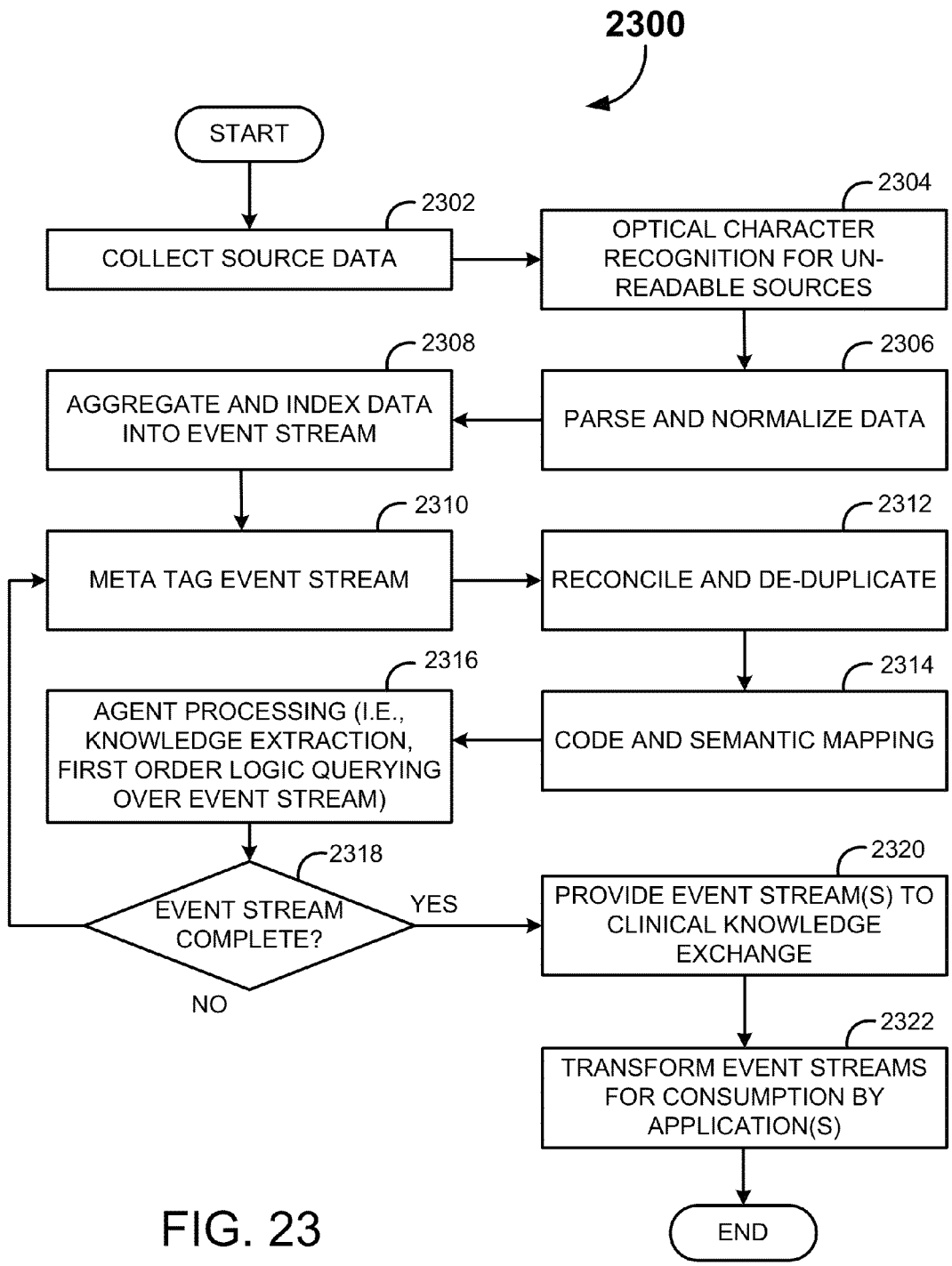
FIG. 23 illustrates a process flow diagram for the generation and utilization of an event stream platform, in accordance with some embodiments.

Now refer to FIG. 23 for a flow diagram 2300 for the process of generating event streams for application consumption. In this example process flow, data sources are collected (at 2302) from a variety of locations, as indicated in the previous figure. Optical character recognition is employed (at 2304) for those records that are not machine readable. All the data is then parsed and normalized (at 2306) and aggregated and indexed (at 2308) to generate a raw event stream.

The raw event stream may be meta tagged (at 2310) and reconciled and de-duplicated (at 2312). The event stream may then be coded and semantics may be mapped (at 2314). The resulting initial event stream may then be provided to one or more agents (at 2316) for processing via knowledge extraction and first order logic querying (as previously discussed).

The resulting event streams may be reprocessed in an iterative fashion for further refinement if a determination is made that the event stream is not final (at 2318). Otherwise, if the event stream is final, then is may be provided to a clinical knowledge exchange (at 2320) for transformation of the event streams for consumption by applications (at 2322).

Applications may provide value to the healthcare organization and patients. For example, a quality optimization application may generate actionable care notifications based upon the event analysis. Population analyzers may be a flexible search and query tool that enables the generation of dashboards for risk assessment, performance, compliance, utilization disease registry, and referral management. HCC optimizer may improve condition capture and risk assessment. It may also monitor coder quality and effort to improve revenue forecasting and reimbursements.

V. Examples

Figure 24:
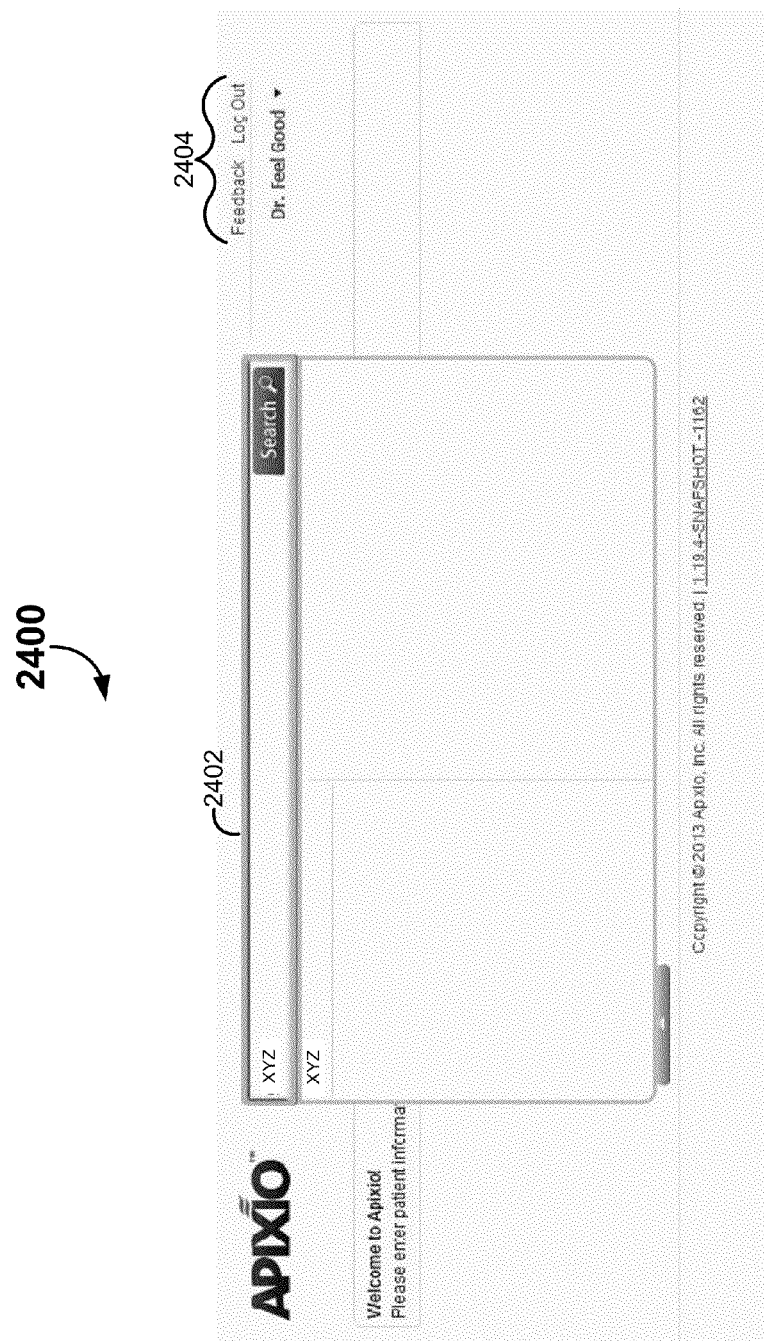
FIGS. 24-33 show example screenshots of an event stream platform, in accordance with some embodiments.

Referring now to FIGS. 24-33, a series of illustrative screenshots are provided which illustrate an interface for the review of event streams in a medical system. In FIG. 24 and initial query screen 2400 is displayed. A search field 2402 is seen, as well as a blank results screen. The physician login information is displayed at 2404. In this example, a search string "xyz" has been entered into the search field. In this example, "xyz" stands for a specific organization.

Figure 25:
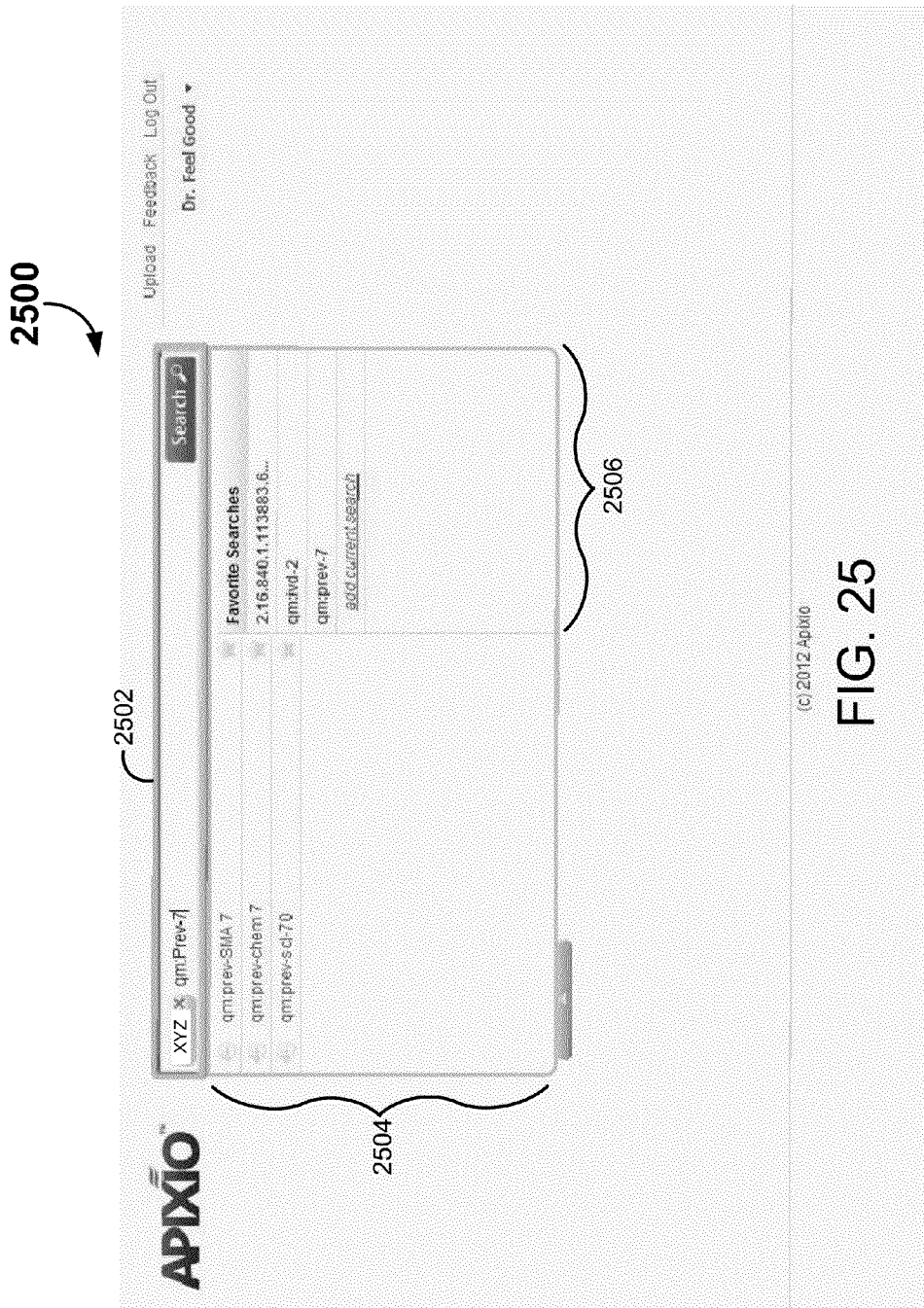

Moving to FIG. 25, a screen 2500 is shown where the string "gwu" has been entered into the search field 2502. Additionally, the user is entering a second term "qm:Prev-7"—A predefined shortcut that evaluates to the numerator and denominator first-order logic query expressions over the event stream, that computes the compliance of the PQRS Prev-7—Influenza Immunization measure in the selected population. Search results are displayed in the display field 2504, and favorite searches are displayed in a sidebar 2506.

Figure 26:
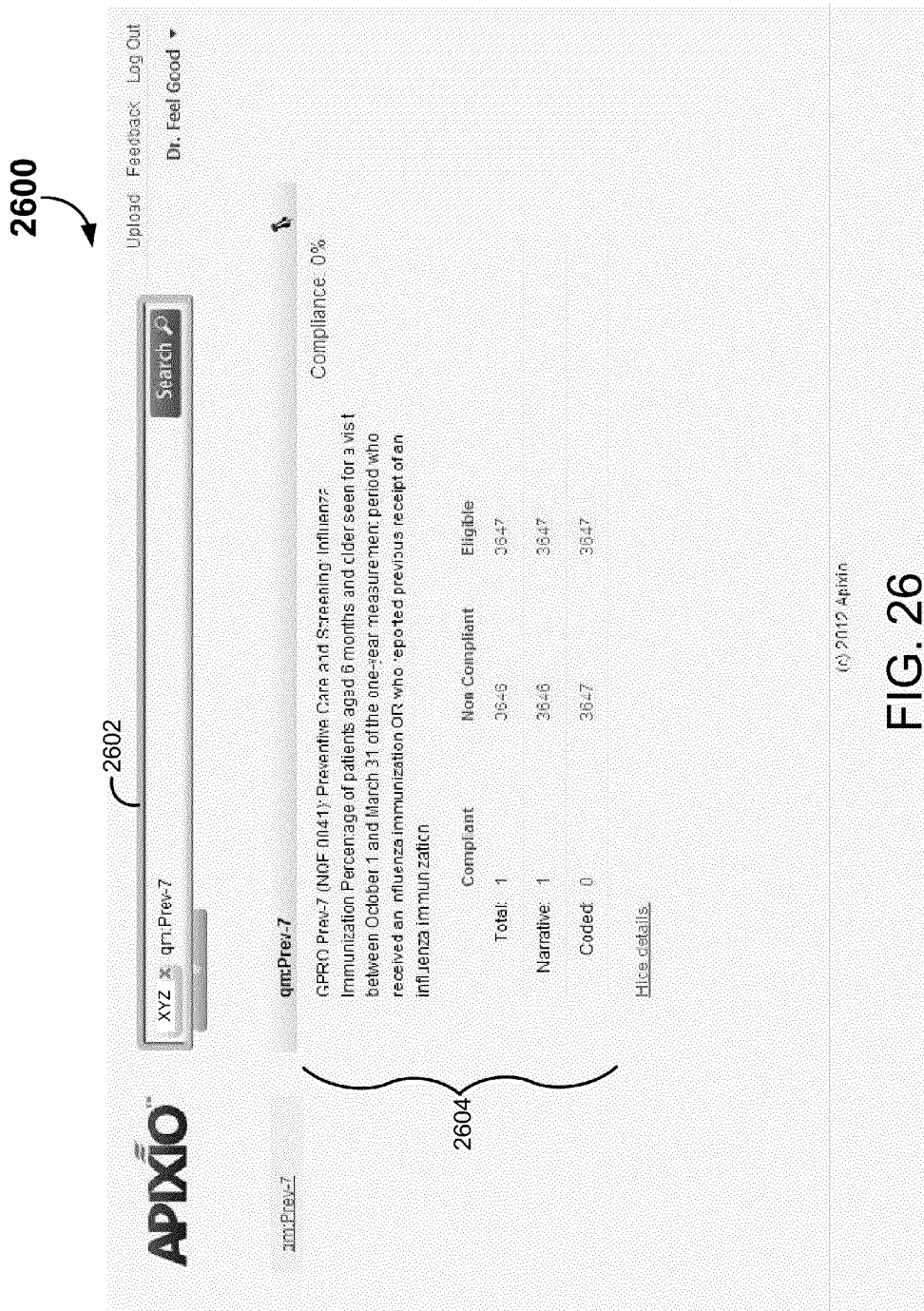
Figure 27:
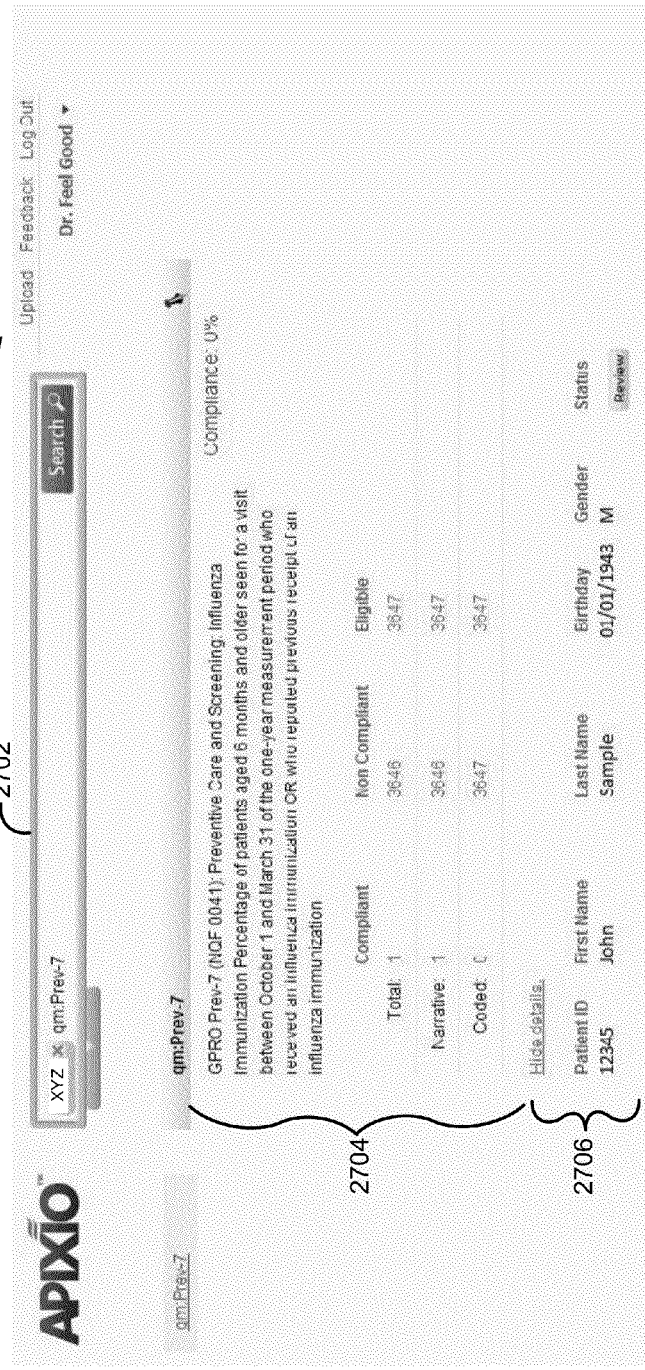

In FIG. 26, a screen 2600 is displayed which illustrates a result for the search string 2602. The results 2604 provide data of compliance for a preventative immunization for influenza. In FIG. 27, the user has expanded one of the records in the results field 2704. The specifics of the record are displayed in a details field 2706. These displays are generated from the event streams. Individual information from the events may be utilized to populate the displayed fields.

Figure 28:
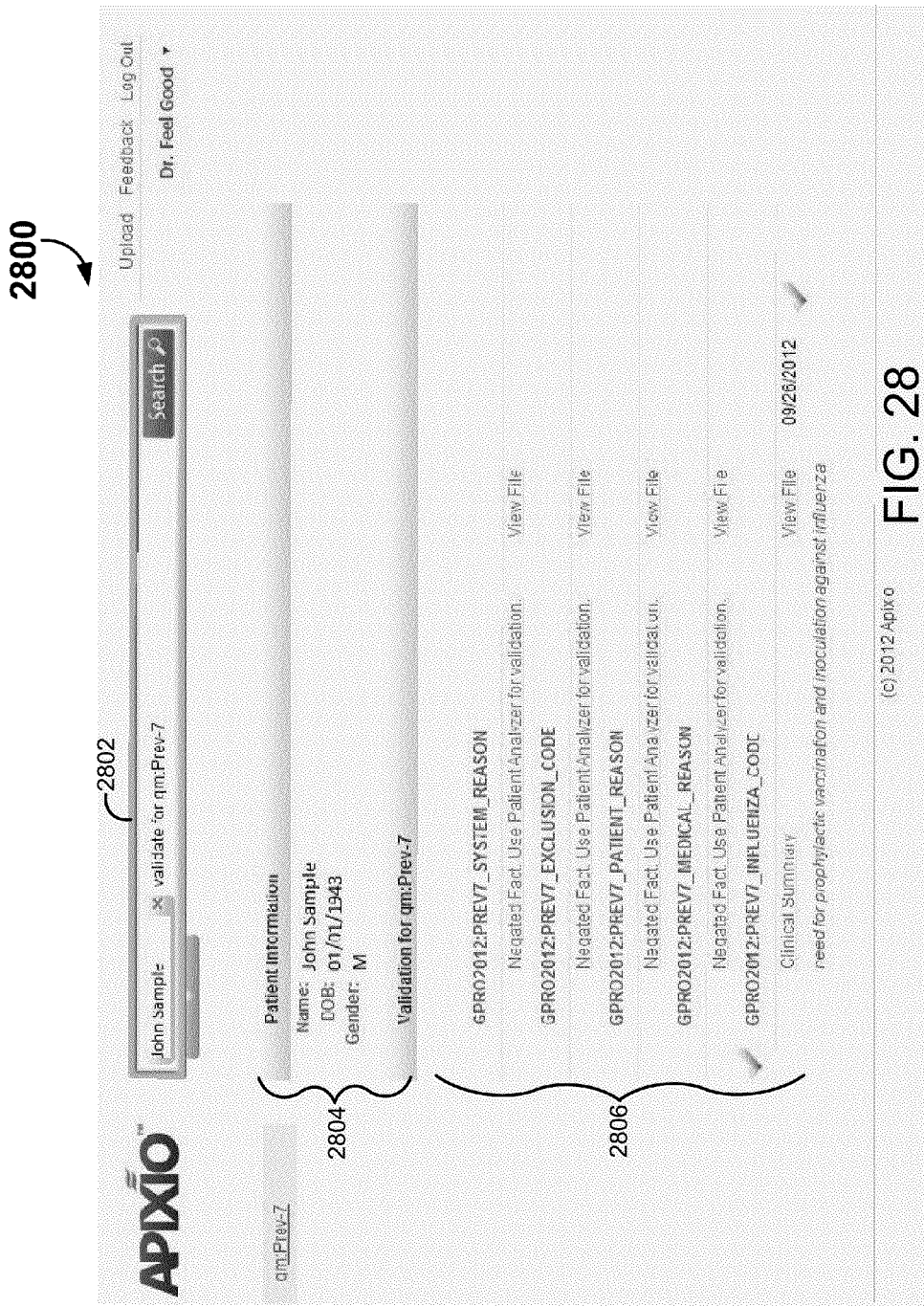

In FIG. 28, the user selects the specific patient (John Sample), by entering him in the search bar 2802, or by selecting the patient from the previous record. Patient information is displayed in a summary field 2804, and the information requested by the physician is displayed below in a results field 2806. In this example the physician requested validation for the earlier finding that John Sample had received influenza preventative care. Events are listed in the results file, including a clinical summary event which validates that the patient had been vaccinated.

Figure 29:
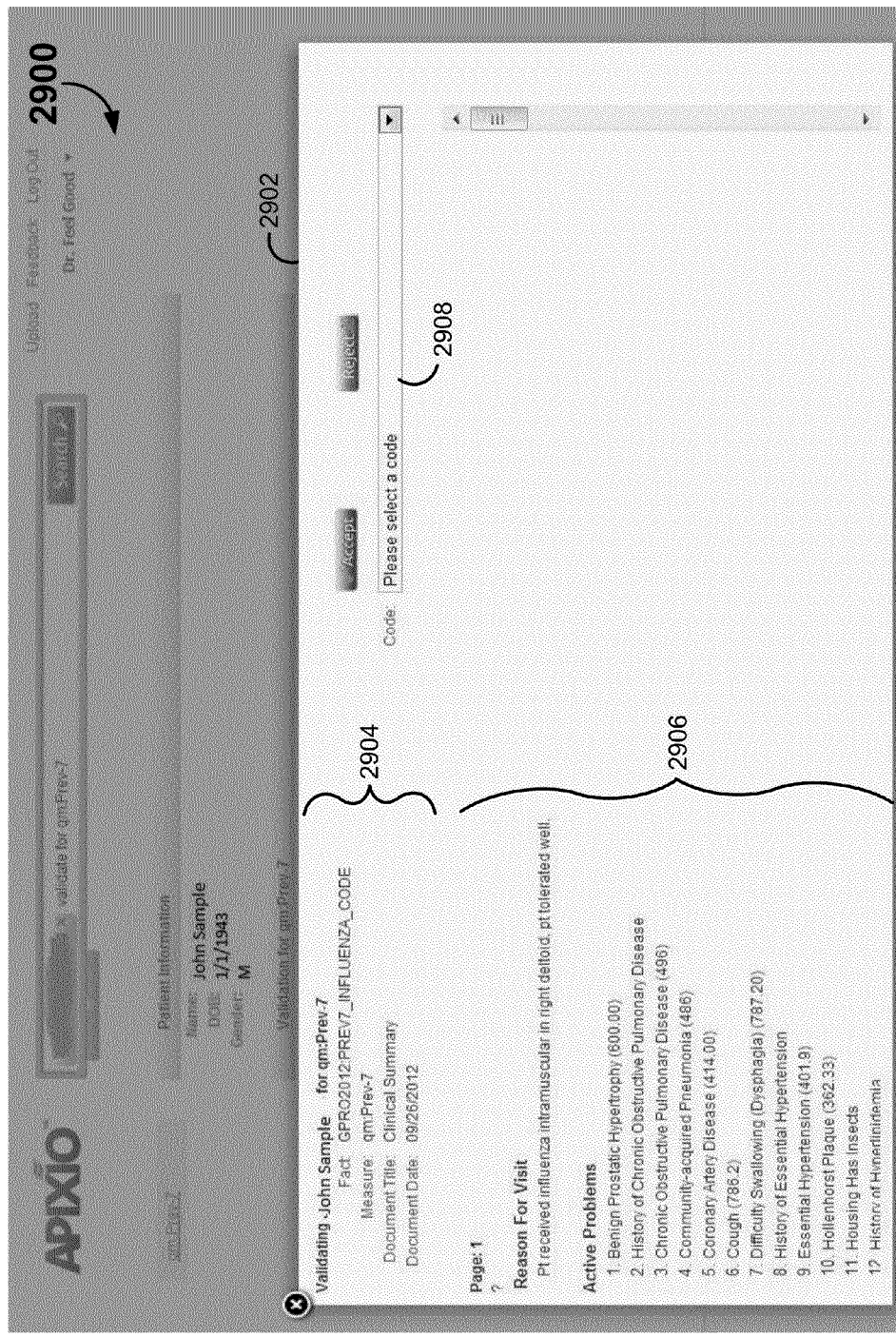

In FIG. 29, a new window 2902 has opened when the physician selects the event. The event summary is provided at the top of the record at 2904, and this application also provides the clinical document at 2906 that was used to generate the event. Lastly, a code dropdown menu 2908 is provided for physician selection.

Figure 30:
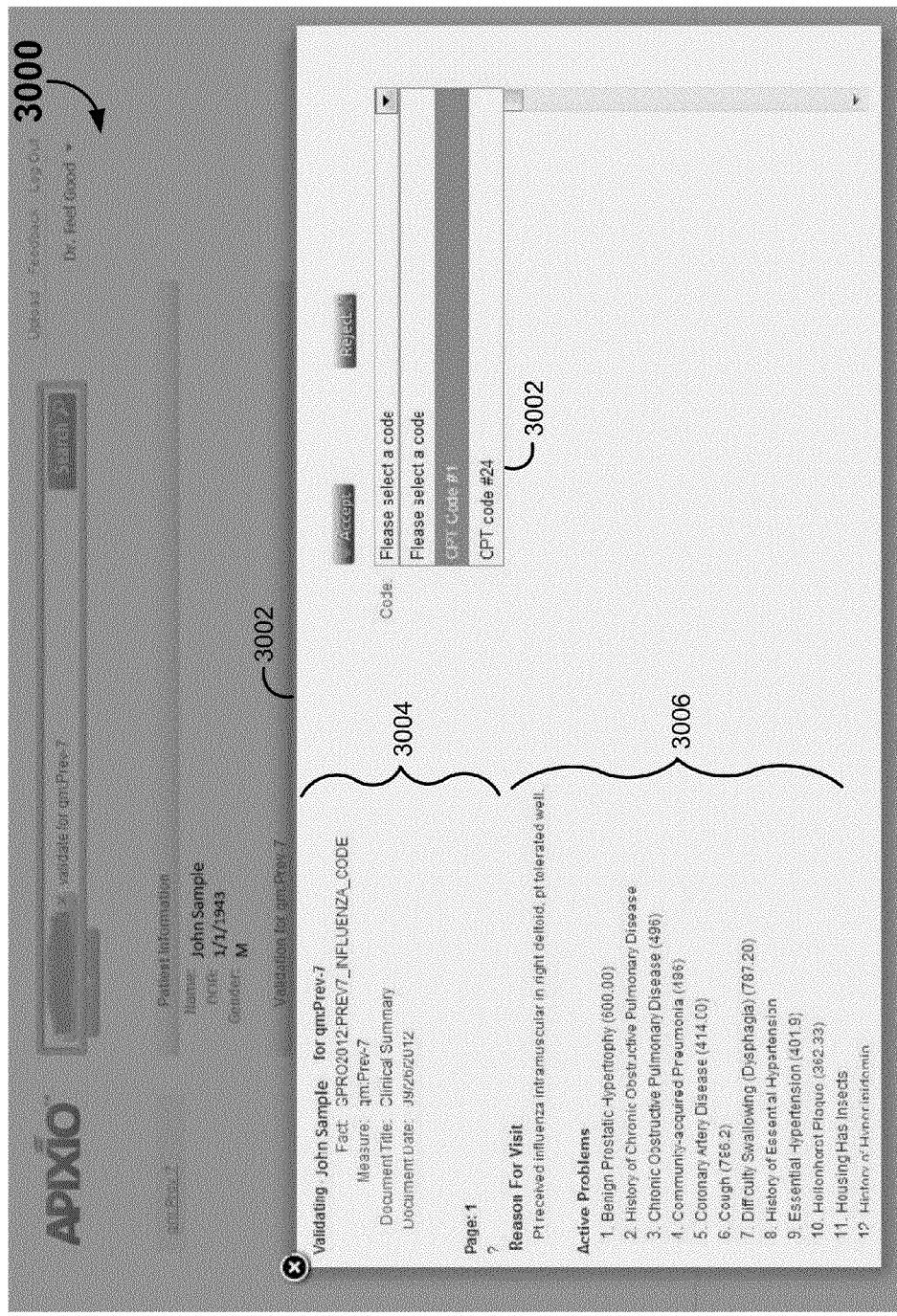

In FIG. 30, the physician has accessed the dropdown menu 3002, and the available codes are presented to the physician. The event summary and clinical document are still shown to the physician at 3004 and 3006, respectively.

Figure 31:
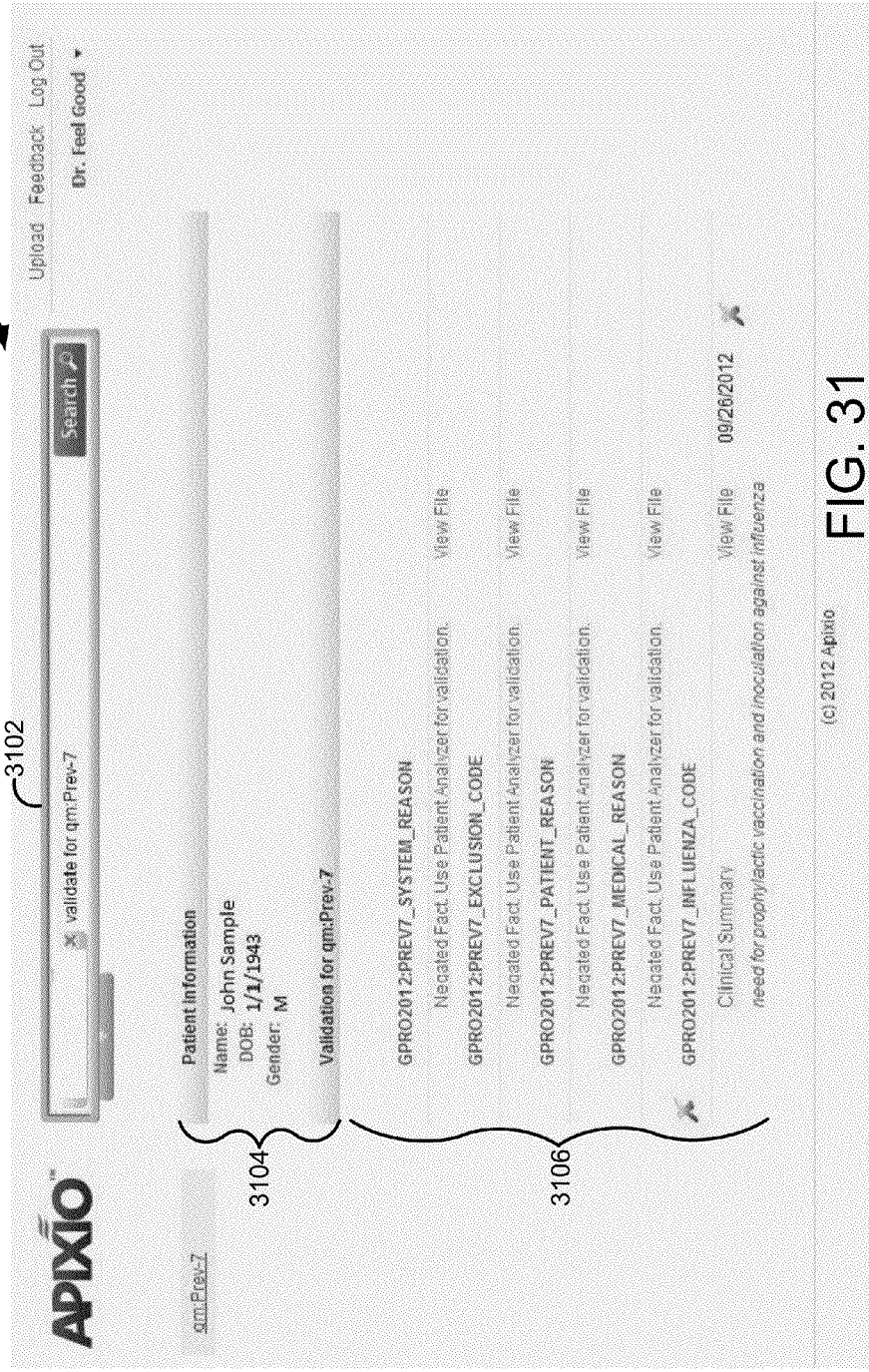

Once the physician has selected and accepted a code, the window closes and the screen 3100 shown in FIG. 31 is now displayed. The search term 3102 and patient summary field 3104 remains unchanged; however, the results field 3106 has been updated to reflect the code selection.

Figure 32:
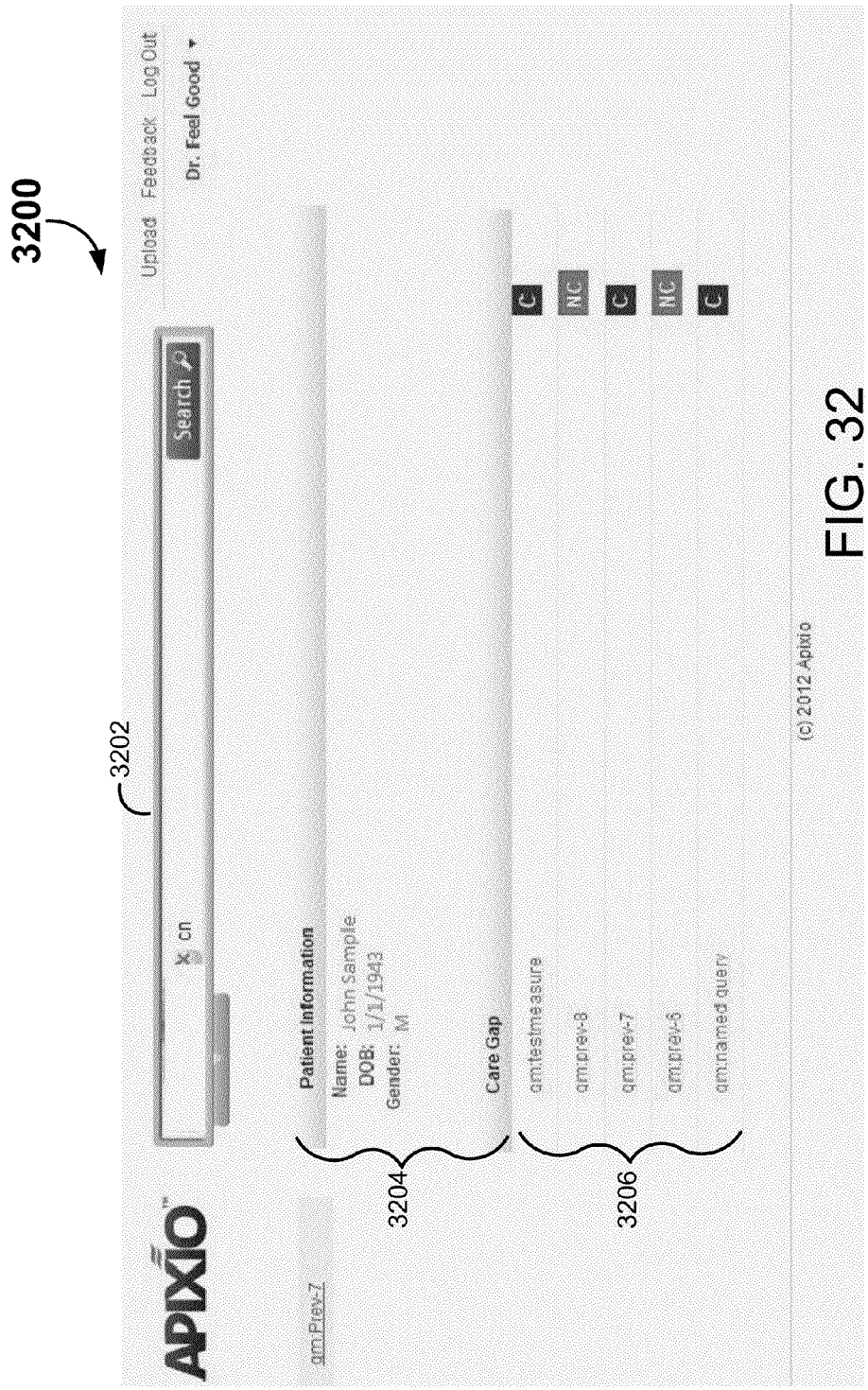

FIG. 32 provides an example screenshot 3200 of the care gap for patient John Sample. A search field 3202 is available for physician navigation, and patient summary information is provided in a top field 3204. Care Gap information is provided in a results field 3206. Various encounters are provided for the patient, and each is listed as either coded or non-coded.

Figure 33:
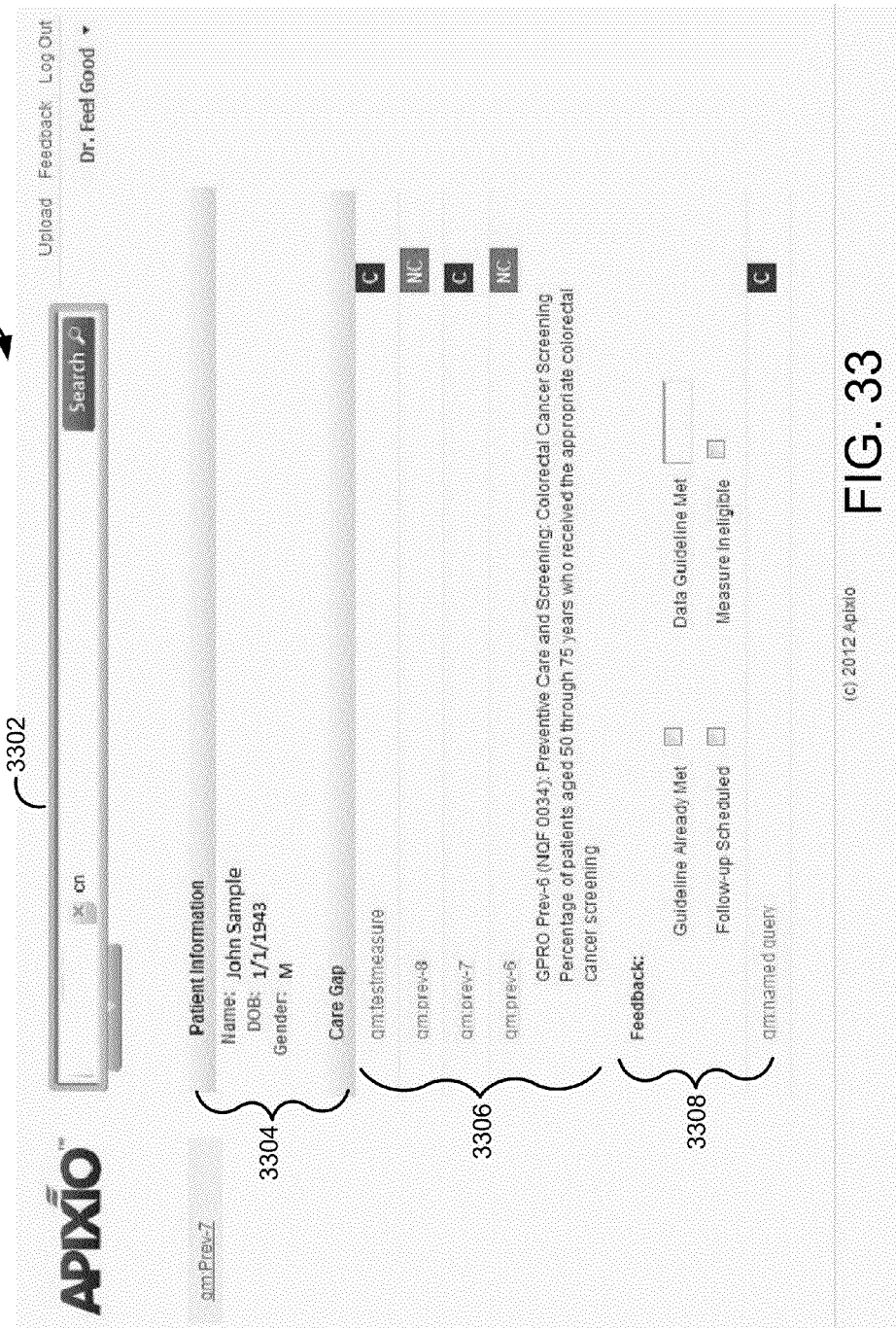

Lastly, FIG. 33 provides a screenshot 3300 where one of the non-compliant records in the results field 3306 has been expanded to provide details and a feedback request 3308 to the physician.

Although the invention has been described in terms of specific embodiments, it is anticipated that alterations and modifications thereof will no doubt become apparent to those skilled in the art. It is therefore intended that the following claims be interpreted as covering all such alterations and modification as fall within the true spirit and scope of the invention.

What is claimed is:

1. In a computerized Medical Information Navigation and Healthcare Reimbursement Engine, a computerized method for generating a final event stream, the method comprising:
collecting medical information from a plurality of data sources;
parsing the medical information;
normalizing the medical information;
indexing the medical information to generate an initial event stream;
semantic meta-tagging the event stream;
iteratively processing the event stream to generate a final event stream using a computerized knowledge extractor, wherein the processing includes at least one of first order logic querying and knowledge extraction to infer at least one additional event which is added to the event stream; and
constructing an optimal patient-claim-encounter vector corresponding to a best case patient encounter from the event stream and computing a payoff corresponding to the best case patient encounter using a computerized healthcare reimbursement processor.

2. The method of claim 1 further comprising providing the final event stream to a clinical knowledge exchange.

3. The method of claim 2 wherein the clinical knowledge exchange transforms the final event stream for consumption by a plurality of applications.

4. The method of claim 3 wherein the applications include internal applications and third party applications.

5. The method of claim 1 further comprising performing optical character recognition on the data sources which are not machine readable.

6. The method of claim 1 wherein the processing is performed by at least one agent.

7. The method of claim 6 wherein the at least one agent includes an internal agent and a third party agent.

8. The method of claim 1 wherein the event comprises a subject, evidence used to infer the event, a fact that was inferred from the evidence, a start date of the event, an end date of the event, an episode level grouping, the source of the event, type of the event, named values, a snippet of the source, an event classification, and expiry information.

9. The method of claim 1 wherein the final event stream is one which does not change after additional iterative processing.

10. A computerized medical information and healthcare reimbursement system for generating a final event stream comprising:
   a data pipeline, including a processor, configured to collect medical information from a plurality of data sources, parse the medical information, normalize the medical information and index the medical information to generate an initial event stream;
   a computerized knowledge extractor configured to semantic meta-tag the event stream, and iteratively process the event stream to generate a final event stream, wherein the processing includes at least one of first order logic querying and knowledge extraction to infer at least one additional event which is added to the event stream; and
   a healthcare reimbursement processor configured to construct an optimal patient-claim-encounter vector corresponding to a best case patient encounter from the event stream and further configured to compute a payoff corresponding to the best case patient encounter.

11. The system of claim 10 further comprising a clinical knowledge exchange configured to transform the final event stream to a format consumable by a plurality of applications.

12. The system of claim 11 wherein the applications include internal applications and third party applications.

13. The system of claim 12 further comprising internal applications.

14. The system of claim 10 wherein the data pipeline is further configured to perform optical character recognition on the data sources which are not machine readable.

15. The system of claim 10 wherein the processing is performed by at least one agent.

16. The system of claim 15 wherein the at least one agent includes an internal agent and a third party agent.

17. The system of claim 10 wherein the event comprises a subject, evidence used to infer the event, a fact that was inferred from the evidence, a start date of the event, an end date of the event, an episode level grouping, the source of the event, type of the event, named values, a snippet of the source, an event classification, and expiry information.

18. The system of claim 10 wherein the final event stream is one which does not change after additional iterative processing.

19. The method of claim 1 wherein the patient-claim-encounter vector is constructed using an equation:

$$P=I*[E_i;E_a];$$

and wherein
   "P" is the payoff;
   "I" is a measure of system intelligence;
   "$[E_i; E_a]$" is the patient-claim-encounter vector;
   "$E_i$" is an efficiency of informational access; and
   "$E_a$" is an efficiency of action.

20. The system of claim 10 wherein the patient-claim-encounter vector is constructed using an equation:

$$P=I*[E_i;E_a];$$

and wherein
   "P" is the payoff;
   "I" is a measure of system intelligence;
   "$[E_i; E_a]$" is the patient-claim-encounter vector;
   "$E_i$" is an efficiency of informational access; and
   "$E_a$" is an efficiency of action.

* * * * *